US012758473B2

(12) United States Patent
Keller et al.

(10) Patent No.: US 12,758,473 B2
(45) Date of Patent: Oct. 13, 2026

(54) SURFACE-TREATED MAGNESIUM OR CALCIUM ION-CONTAINING MATERIALS AS WHITE PIGMENTS IN ORAL CARE COMPOSITIONS

(71) Applicant: Omya International AG, Oftringen (CH)

(72) Inventors: Tobias Keller, Holziken (CH); Tanja Budde, Brittnau (CH); Samuel Rentsch, Spiegel bei Bern (CH)

(73) Assignee: Omya International AG, Oftringen (CH)

( * ) Notice: Subject to any disclaimer, the term of this patent is extended or adjusted under 35 U.S.C. 154(b) by 782 days.

(21) Appl. No.: 17/605,160

(22) PCT Filed: Apr. 22, 2020

(86) PCT No.: PCT/EP2020/061133
§ 371 (c)(1),
(2) Date: Oct. 20, 2021

(87) PCT Pub. No.: WO2020/224957
PCT Pub. Date: Nov. 12, 2020

(65) Prior Publication Data

US 2022/0370310 A1 Nov. 24, 2022

(30) Foreign Application Priority Data

May 3, 2019 (EP) .................................... 19172523
Mar. 20, 2020 (EP) .................................... 20164389

(51) Int. Cl.
*A61K 8/19* (2006.01)
*A61K 8/02* (2006.01)
*A61K 8/21* (2006.01)
*A61Q 11/00* (2006.01)

(52) U.S. Cl.
CPC .............. *A61K 8/19* (2013.01); *A61K 8/0241* (2013.01); *A61K 8/21* (2013.01); *A61Q 11/00* (2013.01); *A61K 2800/92* (2013.01)

(58) Field of Classification Search
None
See application file for complete search history.

(56) References Cited

U.S. PATENT DOCUMENTS 1,361,324 A 12/1920 Grunwald
3,935,304 A 1/1976 Januszewski et al.
4,191,670 A * 3/1980 Strauch .................... C09C 3/08 524/564
4,254,101 A 3/1981 Penny, Jr.
4,303,542 A 12/1981 Heinlein et al.
4,405,599 A 9/1983 Smigel
4,683,157 A 7/1987 Mosser et al.
5,009,809 A 4/1991 Kosin et al.
5,028,252 A 7/1991 Kaes
5,253,660 A 10/1993 Dixit et al.
5,461,101 A * 10/1995 Rothon .................... C08K 3/22 524/436
5,645,821 A 7/1997 Libin
5,979,461 A 11/1999 Bensalem et al.
6,669,928 B1 12/2003 Gurol
8,541,494 B2 * 9/2013 Gane ...................... D21H 19/36 524/425
9,354,180 B2 5/2016 Jiang et al.
2004/0245532 A1 * 12/2004 Maeda ............. C09K 11/77342 257/89
2007/0194276 A1 8/2007 Yuan et al.
2009/0117058 A1 5/2009 Lee et al.

(Continued)

FOREIGN PATENT DOCUMENTS

EP 0077967 A1 5/1983
EP 0335544 A2 10/1989

(Continued)

OTHER PUBLICATIONS

English translation of WO-2014156201-A1 Description (Year: 2014).*
Wang, Y. and Forssberg, E. Dispersants in stirred ball mill grinding. KONA No. 13 (1995) 67-77. (Year: 1995).*
International Search Report and Written Opinion for International Application No. PCT/EP2020/062105 (mailed Jul. 8, 2020).
International Search Report and Written Opinion for International Application No. PCT/EP2020/061133 (mailed Jul. 8, 2020).
International Search Report and Written Opinion for International Application No. PCT/EP2020/061952 (mailed Jun. 17, 2020).

(Continued)

*Primary Examiner* — Anthony J Zimmer
*Assistant Examiner* — Zachary John Baum
(74) *Attorney, Agent, or Firm* — Heslin Rothenberg Farley & Mesiti P.C.

(57) ABSTRACT

The present invention relates to a surface-treated magnesium ion-containing material obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof. The invention further relates to an oral care composition comprising a surface-treated magnesium ion-containing material and/or a surface-treated calcium ion-containing material, as well as the use of a surface-treated magnesium ion-containing material and/or a surface-treated calcium ion-containing material as opacifying agent and/or whitening pigment or for improving the availability of fluoride ions in oral care compositions.

15 Claims, No Drawings

(56) References Cited

U.S. PATENT DOCUMENTS

| | | | | |
|---|---|---|---|---|
| 2010/0322275 | A1* | 12/2010 | Ishii | H01L 33/504 257/E33.056 |
| 2011/0147682 | A1 | 6/2011 | Bown | |
| 2012/0052023 | A1 | 3/2012 | Gane et al. | |
| 2012/0076713 | A1 | 3/2012 | Pust | |
| 2014/0000484 | A1* | 1/2014 | Wilkenhoener | C09C 1/3653 106/447 |
| 2018/0258288 | A1 | 9/2018 | Gerard et al. | |

FOREIGN PATENT DOCUMENTS

| | | | | | |
|---|---|---|---|---|---|
| EP | 0460923 | A2 | | 12/1991 | |
| EP | 0522678 | A2 | * | 1/1993 | C09C 3/063 |
| EP | 0526121 | A1 | | 2/1993 | |
| EP | 1344800 | A1 | | 9/2003 | |
| EP | 2141124 | A1 | | 1/2010 | |
| EP | 2169027 | A1 | * | 3/2010 | C04B 20/107 |
| EP | 2461794 | | | 6/2012 | |
| EP | 2921173 | A1 | * | 9/2015 | A61K 33/10 |
| EP | 2926797 | A1 | | 10/2015 | |
| EP | 3275947 | A1 | | 1/2018 | |
| GB | 544907 | | | 5/1942 | |
| GB | 548197 | | | 9/1942 | |
| GB | 594262 | | | 11/1947 | |
| WO | 2000010520 | A1 | | 3/2000 | |
| WO | 0028977 | A1 | | 5/2000 | |
| WO | 2012031786 | A2 | | 3/2012 | |
| WO | 2012143220 | A1 | | 10/2012 | |
| WO | 2013007571 | A2 | | 1/2013 | |
| WO | 2013034421 | A2 | | 3/2013 | |
| WO | 2013139957 | A1 | | 9/2013 | |
| WO | 2014059678 | A1 | | 4/2014 | |
| WO | 2014148997 | A1 | | 9/2014 | |
| WO | WO-2014156201 | A1 | * | 10/2014 | C09K 11/7734 |
| WO | 2015039994 | A1 | | 3/2015 | |
| WO | 2016198267 | A1 | | 12/2016 | |
| WO | 2017093002 | A1 | | 6/2017 | |
| WO | WO-2017184952 | A1 | * | 10/2017 | C09C 1/02 |
| WO | 2018019710 | A1 | | 2/2018 | |

OTHER PUBLICATIONS

Reddy et al., "EPR, UV-Visible, and Near-Infrared Spectroscopic Characterization of Dolomite", Advances in Condensed Matter Physics, vol. 2008, article ID 175862, 8 pages. 2008.

* cited by examiner

SURFACE-TREATED MAGNESIUM OR CALCIUM ION-CONTAINING MATERIALS AS WHITE PIGMENTS IN ORAL CARE COMPOSITIONS

CROSS REFERENCE TO RELATED APPLICATIONS

This application is a national stage application under 35 U.S.C. § 371 of International Application No. PCT/EP2020/061133, filed on Apr. 22, 2020, and published as WO 2020/224957 A1 on Nov. 12, 2020, which claims priority of European Application No. 19172523.3, filed May 3, 2019, and European Application No. 20164389.7, filed Mar. 20, 2020, which are hereby incorporated by reference in their entirety.

The present invention relates to a surface-treated magnesium ion-containing material obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof. The invention further relates to an oral care composition comprising a surface-treated magnesium ion-containing material and/or a surface-treated calcium ion-containing material, as well as the use of a surface-treated magnesium ion-containing material and/or a surface-treated calcium ion-containing material as opacifying agent and/or whitening pigment or for improving the availability of fluoride ions in oral care compositions.

A wide variety of oral care products is used to clean, protect and groom the tooth and to maintain its structure. For example, WO2000010520A1 refers to a toothpaste comprising, in a liquid or pasty medium, particulate calcium carbonate as the main abrasive cleaning agent, characterized in that the particulate calcium carbonate comprises a mixture of 75-92.5% by weight of the mixture fine of particulate calcium carbonate with a weight average particle size of between 1 and 15 microns, and 7.5-25% by weight of the mixture of coarse particulate calcium carbonate with a weight average particle size of between 30 and 120 microns. EP2461794A2 refers to a toothpaste composition comprising a binder, an abrasive, a foaming agent, water, and polyethylene glycol, wherein said binder comprises semi-refined iota carrageenan. US20090117058A1 refers to a whitening toothpaste composition with improved preservativeness and a sustained tooth whitening effect, characterized by containing peroxide and purified silica. WO2014059678A1 refers to a toothpaste composition comprising: an orally acceptable vehicle, an abrasive comprising calcium carbonate; and a binder system comprising guar gum and at least one cellulose polymer; wherein the binder system is substantially free of magnesium aluminum silicate. U.S. Pat. No. 4,254,101A refers to a toothpaste composition comprising: (A) from about 6% to 45% of a silica dental abrasive; (B) from about 30% to 70% of a humectant; (C) from about 0.03% to 1.0% of a carboxyvinyl polymer; and (D) from about 10% to 45% of water; said composition providing a pH of from about 4.0 to 8.0 when slurried with water in a 3:1 water/composition weight ratio. WO2013007571A2 refers to a toothpaste composition comprising: (i) a calcium based abrasive; (ii) a copolymer of vinylmethyl ether and maleic acid; and, (iii) a clay wherein ratio of said Calcium based abrasive to said copolymer of vinyl methyl ether and maleic anhydride is at least 1:0.0075 and ratio of said calcium based abrasive to said clay is at least 1:0.02. WO2012143220A1 describes a composition that is suitable for remineralisation and whitening of teeth, which comprises a calcium source and regeneration-source calcium salt. A dentifrice composition comprising a water insoluble and/or slightly water-soluble calcium source and an organic acid, or its physiologically acceptable salt, is described in WO2013034421A2. WO2012031786A2 relates to oral care compositions with composite particle actives having a core and a coating, whereby the coating interacts with phosphate ions to produce calcium and phosphate reaction products that are suitable to adhere to tooth enamel and/or dentine to improve the characteristics of teeth.

Usually such products are modified in their appearance in order to satisfy consumer expectations. For example, from a consumer perspective there is a demand for white and opaque products. Currently, titanium dioxide is broadly applied as white pigment in oral care products. For example, U.S. Pat. No. 3,935,304A refers to a toothpaste containing at least about 25% by weight dispersed particles of sodium bicarbonate and a polishing agent system comprising titanium dioxide powder having a particle size less than about two microns, the amount of titanium dioxide particles being more than about 0.1% of the weight of the toothpaste, said particles dispersed in a vehicle containing sufficient liquids, said vehicle consisting essentially of about 5 to 35% water and sufficient viscous water miscible polyol humectant or mixtures thereof, and a sufficient amount of gelling or thickening agent to impart to the toothpaste the pasty consistency, body and the non-tacky nature which is characteristic of conventional dental creams or toothpastes, said sodium bicarbonate being primarily in an undissolved solid state, said dental cream having a granular textured appearance comprising a substantially dispersed non-crystalline appearing granulate of macroscopic crystalline bicarbonate granules in an otherwise smooth continuous matrix.

However, there are strong concerns regarding the use of titanium dioxide in such compositions due to the possible health risks of titanium dioxide and especially of such nanoparticles in said products. Calcium carbonates are also known as white pigments in a wide variety of products. Calcium carbonates such as ground calcium carbonate, precipitated calcium carbonate, and mixtures thereof have a major disadvantage compared to titanium dioxide and thus usually are not considered as material of choice in oral care products. In particular, oral care products are typically provided with fluoride ions for preventing tooth decay and caries. This fluoride may be provided as sodium fluoride. However, fluoride ions strongly absorb on the calcium carbonate surface as calcium fluoride and thus making it unavailable for the interaction with the teeth.

However, the provision of an oral care composition being free of titanium dioxide remains of interest to the skilled man. Furthermore, it is desired to provide an oral care composition providing a sufficient whiteness and/or opacity. Furthermore, it is desired to provide an oral care composition providing a high availability of fluoride ions in the composition, especially compared to compositions comprising calcium carbonate.

Accordingly, it is an object of the present invention to provide an oral care composition, preferably being free of titanium dioxide. A further object of the present invention is to provide an oral care composition providing a sufficient whiteness and/or opacity. A further object of the present invention is to provide an oral care composition providing a high availability of fluoride ions in the composition.

The foregoing objects and other objects are solved by the subject-matter as defined herein in the independent claims.

According to one aspect of the present invention, a surface-treated magnesium ion-containing material is provided, the surface-treated magnesium ion-containing material is obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

According to another aspect of the present invention, an oral care composition is provided, the oral care composition comprising a surface-treated magnesium ion-containing material obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof and/or a surface-treated calcium ion-containing material obtained by treating the surface of a calcium ion-containing material with one or more compound(s) selected from the group consisting of a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

According to a further aspect of the present invention, the use of a surface-treated magnesium ion-containing material and/or a surface-treated calcium ion-containing material as opacifying agent and/or whitening pigment in oral care compositions is provided, wherein the surface-treated magnesium ion-containing material is obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof and/or the surface-treated calcium ion-containing material is obtained by treating the surface of a calcium ion-containing material with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

According to a still further aspect of the present invention, the use of a surface-treated magnesium ion-containing material and/or a surface-treated calcium ion-containing material for improving the availability of fluoride ions in oral care compositions is provided, wherein the surface-treated magnesium ion-containing material is obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof and/or the surface-treated calcium ion-containing material is obtained by treating the surface of a calcium ion-containing material with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof The inventors surprisingly found out that the foregoing surface-treated magnesium ion-containing material and/or surface-treated calcium ion-containing material provides a sufficient whiteness and/or opacity to oral care compositions compared to a composition comprising untreated magnesium and/or calcium ion-containing minerals as white pigment and further provides a high availability of fluoride ions, while it is free of titanium dioxide. More precisely, the inventors found out that the whiteness and/or opacity of an oral care composition can be improved compared to a composition using untreated magnesium and/or calcium ion-containing minerals and further provides a high availability of fluoride ions if a surface-treated magnesium and/or calcium ion-containing material is used in the composition.

Advantageous embodiments of the inventive oral care composition and the use are defined in the corresponding sub-claims.

According to one embodiment, the magnesium ion-containing material is selected from the group consisting of anhydrous magnesium carbonate or magnesite ($MgCO_3$), hydromagnesite ($Mg_5(CO_3)_4(OH)_2 \cdot 4H_2O$), artinite ($Mg_2(CO_3)(OH)_2 \cdot 3H_2O$), dypingite ($Mg_5(CO_3)_4(OH)_2 \cdot 5H_2O$), giorgiosite ($Mg_5(CO_3)_4(OH)_2 \cdot 5H_2O$), pokrovskite ($Mg_2(CO_3)(OH)_2 \cdot 0.5H_2O$), barringtonite ($MgCO_3 \cdot 2H_2O$), lansfordite ($MgCO_3 \cdot 5H_2O$), nesquehonite ($MgCO_3 \cdot 3H_2O$), brucite ($Mg(OH)_2$), dolomite ($CaMg(CO_3)_2$), dolocarbonate and mixtures thereof, preferably selected from anhydrous magnesium carbonate or magnesite ($MgCO_3$), dolomite ($CaMg(CO_3)_2$), hydromagnesite ($Mg_5(CO_3)_4(OH)_2 \cdot 4H_2O$), brucite ($Mg(OH)_2$) and mixtures thereof.

According to another embodiment, the magnesium ion-containing material is in form of particles having a) a volume median grain diameter ($d_{50}$) of ≥150 nm, preferably from 150 nm to 40 μm, more preferably from 0.2 to 35 μm, even more preferably from 0.3 to 30 μm, and most preferably from 0.4 to 27 μm, as determined by laser diffraction, and/or b) a volume determined top cut particle size ($d_{98}$) of equal to or less than 100 μm, preferably from 1 to 90 μm, more preferably from 1.5 to 85 μm, and most preferably from 1.5 to 80 μm, as determined by laser diffraction.

According to another embodiment, the magnesium ion-containing material is in form of particles having a BET specific surface area in the range from 2 to 200 $m^2/g$, preferably from 2 to 100 $m^2$/g, and most preferably from 3 to 75 $m^2$/g, measured using nitrogen and the BET method according to ISO 9277:2010.

According to yet another embodiment, the magnesium ion-containing material contains up to 25 000 ppm $Ca^{2+}$ ions.

According to one embodiment, the surface-treated magnesium ion-containing material is obtained by treating the surface of the magnesium ion-containing material with the one or more compound(s) in an amount from 0.1 to 25 wt.-%, based on the total dry weight of the magnesium ion-containing material.

According to another embodiment, the silicate- and/or aluminate-group containing compound is selected from the group comprising alkali metal silicates, alkali metal aluminates, silicon alkoxides and aluminium alkoxides, preferably from sodium silicate, potassium silicate, sodium aluminate, potassium aluminate, tetramethyl orthosilicate, tetraethyl orthosilicate, aluminium methoxide, aluminium ethoxide, aluminium isopropoxide, and mixtures thereof, and more preferably from sodium silicate, tetraethyl orthosilicate, and aluminium isopropoxide.

According to one embodiment of the oral care composition, the oral care composition further comprises a fluoride compound, preferably the fluoride compound is selected from the group consisting of sodium fluoride, stannous fluoride, sodium monofluorophosphate, potassium fluoride, potassium stannous fluoride, sodium fluorostannate, stannous chlorofluoride, amine fluoride, and mixtures thereof, and more preferably the fluoride compound is sodium monofluorophosphate and/or sodium fluoride.

According to another embodiment of the oral care composition, the oral care composition further comprises a remineralisation and/or whitening agent, preferably selected from the group consisting of silica, hydroxylapatite, e.g. nano-hydroxylapatite, calcium carbonate, e.g. amorphous calcium carbonate, ground calcium carbonate, precipitated calcium carbonate, surface-reacted calcium carbonate and combinations thereof, calcium silicate and mixtures thereof.

According to yet another embodiment of the oral care composition, the oral care composition is a toothpaste, a toothgel, a toothpowder, a varnish, an adhesive gel, a cement, a resin, a spray, a foam, a balm, a composition carried out on a mouthstrip or a buccal adhesive patch, a chewable tablet, a chewable pastille, a chewable gum, a lozenge, a beverage, or a mouthwash, preferably a chewable gum, a lozenge, a toothpaste, a toothpowder, or a mouthwash, and most preferably a toothpaste.

According to one embodiment of the oral care composition, the oral care composition has a pH between 6.8 and 10, preferably between 7.5 and 9 and most preferably between 8 and 9.

According to another embodiment of the oral care composition, the oral care composition comprises the surface-treated magnesium ion-containing material and/or the surface-treated calcium ion-containing material in an amount from 0.1 to 40 wt.-%, preferably from 0.5 to 10 wt.-%, based on the total weight of the composition.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

In the following, preferred embodiments of the inventive oral care composition will be set out in more detail. It is to be understood that these embodiments and details also apply to the inventive use as far as applicable.

Surface-Treated Magnesium Ion-Containing Material

According to the present invention, a surface-treated magnesium ion-containing material is provided. The surface-treated magnesium ion-containing material is obtained by treating the surface of a magnesium ion-containing material with one or more compound(s) selected from the group consisting of phosphoric acid, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound and a corresponding salt thereof.

It is appreciated that the term "magnesium ion-containing material" refers to a material that comprises at least 38 wt.-% of a magnesium compound. In one embodiment, the magnesium ion-containing material comprises at least 38 wt.-%, preferably between 38 and 100 wt.-%, more preferably between 38 and 99.95 wt.-%, e.g. from 38 to 55 wt.-%, based on the total dry weight of the material, of the magnesium compound. In another embodiment, the magnesium ion-containing material comprises at least 85 wt.-%, preferably between 85 and 100 wt.-%, more preferably between 90 and 99.95 wt.-%, based on the total dry weight of the material, of the magnesium compound. Thus, it is to be noted that the magnesium ion-containing material may further comprise impurities typically associated with the type of material used. For example, the magnesium ion-containing material may further comprise impurities such as calcium ion-containing materials like calcium hydroxide, calcium carbonate and mixtures thereof.

For example, if the magnesium ion-containing material comprises the magnesium compound in an amount of at least 38 wt.-%, preferably between 38 and 100 wt.-%, more preferably between 38 and 99.95 wt.-%, e.g. from 38 to 45 wt.-%, based on the total dry weight of the material, the impurities such as calcium ion-containing materials like calcium hydroxide, calcium carbonate and mixtures thereof are present in amounts of less than 62 wt.-%, preferably between 0 and 62 wt.-%, more preferably between 0.05 and 62 wt.-%, e.g. from 45 to 62 wt.-%, based on the total dry weight of the material. If the magnesium ion-containing material comprises the magnesium compound in an amount of at least 85 wt.-%, preferably between 85 and 100 wt.-%, more preferably between 90 and 99.95 wt.-%, based on the total dry weight of the material, the impurities such as calcium ion-containing materials like calcium hydroxide, calcium carbonate and mixtures thereof are present in amounts of less than 15 wt.-% and most preferably from 0.05 to 10 wt.-%, based on the total dry weight of the material. It is further appreciated that the magnesium ion-containing material may be a mineral phase comprising calcium and magnesium ions, such as dolomite ($MgCa(CO_3)_2$).

The magnesium ion-containing material can be a naturally occurring or synthetic magnesium ion-containing material.

According to one embodiment of the present invention the naturally occurring magnesium ion-containing material may be obtained by dry grinding. According to another embodiment of the present invention, the naturally occurring magnesium ion-containing material may be obtained by wet grinding and optionally subsequent drying.

In general, the grinding step can be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the magnesium ion-containing material is obtained by wet-grinding, the grinding step may be performed under conditions such that autogenous grinding takes place and/or by horizontal ball milling, and/or other such processes known to the skilled man. The wet processed ground magnesium ion-containing material thus obtained may be washed and dewatered by well-known processes, e.g. by flocculation, filtration or forced evaporation prior to drying. The subsequent step of drying may be carried out in a single step such as spray drying, or in at least two steps. It is also common that such a mineral material undergoes a beneficiation step (such as a flotation, bleaching or magnetic separation step) to remove impurities.

Synthetic magnesium ion-containing materials in the meaning of the present invention can be obtained by processes well known in the art. For instance, U.S. Pat. No. 1,361,324, U.S. Pat. No. 935,418, GB548197 and GB544907 generally describe the formation of aqueous solutions of magnesium bicarbonate (typically described as "$Mg(HCO3)_2$"), which is then transformed by the action of a base, e.g., magnesium hydroxide, to form hydromagnesite. Other processes described in the art suggest to prepare compositions containing both, hydromagnesite and magnesium hydroxide, wherein magnesium hydroxide is mixed with water to form a suspension which is further contacted with carbon dioxide and an aqueous basic solution to form the corresponding mixture; cf. for example U.S. Pat. No. 5,979,461. EP0526121 describes a calcium-magnesium carbonate composite consisting of calcium carbonate and magnesium carbonate hydroxide and a method for the preparation thereof. Furthermore, GB594262 relates to a method and apparatus for treating magnesia-containing materials, such as magnesium and calcium carbonate materials for obtaining respective carbonates in discrete and separate forms, by controlled carbonation such that the magnesium and calcium carbonates may be separated by mechanical means and with attainment of special utilities in separated products. US2007194276 describes a method of reductively bleaching a mineral slurry comprising adding in the mineral slurry an effective amount of a formamidine sulfinic acid (FAS) and an effective amount of a borohydride to reductively bleach the mineral slurry.

For example, the magnesium ion-containing material encompasses a naturally occurring or synthetic magnesium ion-containing material selected from the group consisting of anhydrous magnesium carbonate or magnesite ($MgCO_3$), hydromagnesite ($Mg_5(CO_3)_4(OH)_2 \cdot 4H_2O$), artinite ($Mg_2(CO_3)(OH)_2 \cdot 3H_2O$), dypingite ($Mg_5(CO_3)_4(OH)_2 \cdot 5H_2O$), giorgiosite ($Mg_5(CO_3)_4(OH)_2 \cdot 5H_2O$), pokrovskite ($Mg_2(CO_3)(OH)_2 \cdot 0.5H_2O$), barringtonite ($MgCO_3 \cdot 2H_2O$), lansfordite ($MgCO_3 \cdot 5H_2O$), nesquehonite ($MgCO_3 \cdot 3H_2O$), brucite ($Mg(OH)_2$), dolomite ($CaMg(CO_3)_2$), dolocarbonate and mixtures thereof, preferably selected from anhydrous magnesium carbonate or magnesite ($MgCO_3$), dolomite ($CaMg(CO_3)_2$), hydromagnesite ($Mg_5(CO_3)_4(OH)_2 \cdot 4H_2O$), brucite ($Mg(OH)_2$) and mixtures thereof.

In the meaning of the present invention, the term "dolocarbonate" refers to a composite material comprising a magnesium mineral, preferably hydromagnesite ($Mg_5(CO_3)_4(OH)_2 \cdot 4H_2O$), and calcium carbonate agglomerated at primary particle level. Such dolocarbonates are for examples described in WO2013139957A1 and WO2015039994 A1, which are thus incorporated by references.

Preferably, the magnesium ion-containing material encompasses a naturally occurring or synthetic magnesium ion-containing material selected from the group consisting of anhydrous magnesium carbonate or magnesite ($MgCO_3$), hydromagnesite ($Mg_5(CO_3)_4(OH)_2 \cdot 4H_2O$), nesquehonite ($MgCO_3 \cdot 3H_2O$), brucite ($Mg(OH)_2$), dolomite ($CaMg(CO_3)_2$), dolocarbonate and mixtures thereof. For example, the magnesium ion-containing material comprises the naturally occurring or synthetic magnesium carbonate selected from the group consisting of anhydrous magnesium carbonate or magnesite ($MgCO_3$), hydromagnesite ($Mg_5(CO_3)_4(OH)_2 \cdot 4H_2O$), nesquehonite ($MgCO_3 \cdot 3H_2O$), brucite ($Mg(OH)_2$), dolomite ($CaMg(CO_3)_2$), dolocarbonate and mixtures thereof in an amount of at least 80 wt.-%, more preferably at least 85 wt.-%, even more preferably between 85 and 100 wt.-%, and most preferably between 90 and 99.95 wt.-%, based on the total dry weight of the material.

In one embodiment, the magnesium ion-containing material comprises anhydrous magnesium carbonate or magnesite ($MgCO_3$) and/or dolomite ($CaMg(CO_3)_2$) and/or hydromagnesite ($Mg_5(CO_3)_4(OH)_2 \cdot 4H_2O$) and/or brucite ($Mg(OH)_2$), preferably synthetic hydromagnesite ($Mg_5(CO_3)_4(OH)_2 \cdot 4H_2O$) and/or brucite ($Mg(OH)_2$) and/or naturally occurring anhydrous magnesium carbonate or magnesite ($MgCO_3$) and/or dolomite ($CaMg(CO_3)_2$). Preferably, the magnesium ion-containing material comprises anhydrous magnesium carbonate or magnesite ($MgCO_3$) and/or dolomite ($CaMg(CO_3)_2$) and/or hydromagnesite ($Mg_5(CO_3)_4(OH)_2 \cdot 4H_2O$) and/or brucite ($Mg(OH)_2$), preferably synthetic hydromagnesite ($Mg_5(CO_3)_4(OH)_2 \cdot 4H_2O$) and/or brucite ($Mg(OH)_2$) and/or naturally occurring anhydrous magnesium carbonate or magnesite ($MgCO_3$) and/or dolomite ($CaMg(CO_3)_2$), in an amount of at least 80 wt.-%, more preferably at least 85 wt.-%, even more preferably between 85 and 100 wt.-%, and most preferably between 90 and 99.95 wt.-%, based on the total dry weight of the material.

For example, the magnesium ion-containing material comprises anhydrous magnesium carbonate or magnesite ($MgCO_3$) or dolomite ($CaMg(CO_3)_2$) or hydromagnesite ($Mg_5(CO_3)_4(OH)_2 \cdot 4H_2O$) or brucite ($Mg(OH)_2$), e.g. synthetic hydromagnesite ($Mg_5(CO_3)_4(OH)_2 \cdot 4H_2O$) or brucite ($Mg(OH)_2$) or naturally occurring anhydrous magnesium carbonate or magnesite ($MgCO_3$) or dolomite ($CaMg(CO_3)_2$). For example, the magnesium ion-containing material comprises anhydrous magnesium carbonate or magnesite ($MgCO_3$), e.g. naturally occurring anhydrous magnesium carbonate or magnesite ($MgCO_3$). Alternatively, the magnesium ion-containing material comprises dolomite ($CaMg(CO_3)_2$), e.g. naturally occurring dolomite (CaMg $(CO_3)_2$). In one embodiment, the magnesium ion-containing material comprises anhydrous magnesium carbonate or magnesite ($MgCO_3$) or dolomite ($CaMg(CO_3)_2$) or hydromagnesite ($Mg_5(CO_3)_4(OH)_2 \cdot 4H_2O$) or brucite ($Mg(OH)_2$), e.g. synthetic hydromagnesite ($Mg_5(CO_3)_4(OH)_2 \cdot 4H_2O$) or brucite ($Mg(OH)_2$) or naturally occurring anhydrous magnesium carbonate or magnesite ($MgCO_3$) or dolomite ($CaMg(CO_3)_2$), in an amount of at least 80 wt.-%, more preferably at least 85 wt.-%, even more preferably between 85 and 100 wt.-%, and most preferably between 90 and 99.95 wt.-%, based on the total dry weight of the material.

In one embodiment, the magnesium ion-containing material consists of anhydrous magnesium carbonate or magnesite ($MgCO_3$) and/or dolomite ($CaMg(CO_3)_2$), e.g. naturally occurring anhydrous magnesium carbonate or magnesite ($MgCO_3$) or dolomite ($CaMg(CO_3)_2$).

In an alternative embodiment, the magnesium ion-containing material consists of hydromagnesite ($Mg_5(CO_3)_4(OH)_2 \cdot 4H_2O$) or brucite ($Mg(OH)_2$), e.g. synthetic hydromagnesite ($Mg_5(CO_3)_4(OH)_2 \cdot 4H_2O$) or brucite ($Mg(OH)_2$), preferably hydromagnesite ($Mg_5(CO_3)_4(OH)_2 \cdot 4H_2O$), e.g. synthetic hydromagnesite ($Mg_5(CO_3)_4(OH)_2 \cdot 4H_2O$).

Preferably, the magnesium ion-containing material comprises, preferably consists of, dolomite ($CaMg(CO_3)_2$), e.g. naturally occurring dolomite ($CaMg(CO_3)_2$).

It is appreciated that the magnesium ion-containing material is preferably provided as particles not being in the nanosized range. It is thus preferred that the magnesium ion-containing material does not comprise particles having a primary particle size of <100 nm.

In general, the magnesium ion-containing material is in form of particles having a volume median grain diameter ($d_{50}$) of ≥150 nm, preferably from 150 nm to 40 μm, more preferably from 0.2 to 35 μm, even more preferably from 0.3 to 30 μm, and most preferably from 0.4 to 27 μm, as determined by laser diffraction.

According to one embodiment of the present invention, the magnesium ion-containing material is in form of particles having a volume median grain diameter ($d_{50}$) of ≥150 nm, preferably from 150 nm to 20 μm, more preferably from 0.2 to 15 μm, even more preferably from 0.3 to 10 μm, and most preferably from 0.4 to 5 μm, as determined by laser diffraction. Alternatively, the magnesium ion-containing material is in form of particles having a volume median grain diameter ($d_{50}$) of ≥150 nm, preferably from 150 nm to 20 μm, more preferably from 0.2 to 15 μm, even more preferably from 0.5 to 10 μm, and most preferably from 1 to 5 μm, as determined by laser diffraction.

According to a further embodiment of the present invention, the magnesium ion-containing material is in form of particles having a volume determined top cut particle size ($d_{98}$) of equal to or less than 100 μm, preferably from 1 to 90 μm, more preferably from 1.5 to 85 μm, and most preferably from 1.5 to 80 μm, as determined by laser diffraction. For example, the magnesium ion-containing material is in form of particles having a volume determined top cut particle size ($d_{98}$) of equal to or less than 30 μm, preferably from 1 to 30 μm, more preferably from 1.5 to 20 μm, and most preferably from 1.5 to 18 μm, as determined by laser diffraction. Alternatively, the magnesium ion-containing material is in form of particles having a volume determined top cut particle size ($d_{98}$) of equal to or less than 30 μm, preferably from 2 to 30 μm, more preferably from 5 to 20 μm, and most preferably from 8 to 18 μm, as determined by laser diffraction.

Thus, the magnesium ion-containing material is in form of particles preferably having a) a volume median grain diameter ($d_{50}$) of ≥150 nm, preferably from 150 nm to 40 μm, more preferably from 0.2 to 35 μm, even more preferably from 0.3 to 30 μm, and most preferably from 0.4 to 27 μm, as determined by laser diffraction, and b) a volume determined top cut particle size ($d_{98}$) of equal to or less than 100 μm, preferably from 1 to 90 μm, more preferably from 1.5 to 85 μm, and most preferably from 1.5 to 80 μm, as determined by laser diffraction.

In one embodiment, the magnesium ion-containing material is in form of particles having a volume median grain diameter ($d_{50}$) in the range from 0.4 to 27 μm, as determined by laser diffraction, and a volume determined top cut particle size ($d_{98}$) in the range from 1.5 to 80 μm, as determined by laser diffraction.

In an alternative embodiment, the magnesium ion-containing material is in form of particles having a volume median grain diameter ($d_{50}$) in the range from 0.4 to 5 μm, as determined by laser diffraction, and a volume determined top cut particle size ($d_{98}$) in the range from 1.5 to 18 μm, as determined by laser diffraction.

Alternatively, the magnesium ion-containing material is in form of particles having a volume median grain diameter ($d_{50}$) in the range from 1 to 5 μm, as determined by laser diffraction, and a volume determined top cut particle size ($d_{98}$) in the range from 8 to 18 μm, as determined by laser diffraction.

For example, the magnesium ion-containing material comprises anhydrous magnesium carbonate or magnesite ($MgCO_3$) or dolomite ($CaMg(CO_3)_2$) or hydromagnesite ($Mg_5(CO_3)_4(OH)_2 \cdot 4H_2O$) or brucite ($Mg(OH)_2$), e.g. synthetic hydromagnesite ($Mg_5(CO_3)_4(OH)_2 \cdot 4H_2O$) or brucite ($Mg(OH)_2$) or naturally occurring anhydrous magnesium carbonate or magnesite ($MgCO_3$) or dolomite ($CaMg(CO_3)_2$), and has a volume median grain diameter ($d_{50}$) in the range from 0.4 to 27 μm, as determined by laser diffraction, and a volume determined top cut particle size ($d_{98}$) in the range from 1.5 to 80 μm, as determined by laser diffraction.

Preferably, the magnesium ion-containing material comprises dolomite ($CaMg(CO_3)_2$), e.g. naturally occurring dolomite ($CaMg(CO_3)_2$), and has a volume median grain diameter ($d_{50}$) in the range from 0.4 to 27 μm or from 0.4 to 5 μm, as determined by laser diffraction, and a volume determined top cut particle size ($d_{98}$) in the range from 1.5 to 80 μm or from 1.5 to 18 μm, as determined by laser diffraction.

In one embodiment, the magnesium ion-containing material comprises anhydrous magnesium carbonate or magnesite ($MgCO_3$) or dolomite ($CaMg(CO_3)_2$) or hydromagnesite ($Mg_5(CO_3)_4(OH)_2 \cdot 4H_2O$) or brucite ($Mg(OH)_2$), e.g. synthetic hydromagnesite ($Mg_5(CO_3)_4(OH)_2 \cdot 4H_2O$) or brucite ($Mg(OH)_2$) or naturally occurring anhydrous magnesium carbonate or magnesite ($MgCO_3$) or dolomite ($CaMg(CO_3)_2$), in an amount of at least 80 wt.-%, more preferably at least 85 wt.-%, even more preferably between 85 and 100 wt.-%, and most preferably between 90 and 99.95 wt.-%, based on the total dry weight of the material and has a volume median grain diameter ($d_{50}$) in the range from 0.4 to 27 μm, as determined by laser diffraction, and a volume determined top cut particle size ($d_{98}$) in the range from 1.5 to 80 μm, as determined by laser diffraction.

Preferably, the magnesium ion-containing material comprises dolomite ($CaMg(CO_3)_2$), e.g. naturally occurring dolomite ($CaMg(CO_3)_2$), in an amount of at least 80 wt.-%, more preferably at least 85 wt.-%, even more preferably between 85 and 100 wt.-%, and most preferably between 90 and 99.95 wt.-%, based on the total dry weight of the material and has a volume median grain diameter ($d_{50}$) in the range from 0.4 to 27 μm or from 4 to 5 μm, as determined by laser diffraction, and a volume determined top cut particle size ($d_{98}$) in the range from 1.5 to 80 μm or from 1.5 to 18 μm, as determined by laser diffraction.

Throughout the present document, the "particle size" of a magnesium ion-containing material is described by its distribution of particle sizes on a volume base. Volume determined median grain diameter $d_{50}$ (or $d_{50}$(vol)) and the volume determined top cut particle size $d_{98}$ (or $d_{98}$(vol)) was evaluated using a Malvern Mastersizer 3000 Laser Diffraction System (Malvern Instruments Plc., Great Britain) equipped with a Hydro LV system. The $d_{50}$(vol) or $d_{98}$(vol) value indicates a diameter value such that 50% or 98% by volume, respectively, of the particles have a diameter of less than this value. The powders were suspended in 0.1 wt.-% $Na_4O_7P_2$ solution. 10 mL of 0.1 wt.-% $Na_4O_7P_2$ was added to the Hydro LV tank, then the sample slurry was introduced until an obscuration between 10-20% was achieved. Measurements were conducted with red and blue light for 10 s each. For the analysis of the raw data, the models for non-spherical particle sizes using Mie theory was utilized, and a particle refractive index of 1.57, a density of 2.70 g/cm$^3$, and an absorption index of 0.005 was assumed. The methods and instruments are known to the skilled person and are commonly used to determine particle size distributions of fillers and pigments.

Additionally or alternatively, the magnesium ion-containing material has a whiteness determined as CIELAB L* of >90%, preferably >95%, more preferably >98% and most preferably >98.5% and measured dry according to EN ISO 11664 4:2010.

In one embodiment, the magnesium ion-containing material is in form of particles having a BET specific surface area in the range from 2 to 200 m$^2$/g, preferably from 2 to 100 m$^2$/g, and most preferably from 3 to 75 m$^2$/g, measured using nitrogen and the BET method according to ISO 9277:2010.

The "specific surface area" (expressed in m$^2$/g) of a material as used throughout the present application can be determined by the Brunauer Emmett Teller (BET) method with nitrogen as adsorbing gas and by use of a ASAP 2460 instrument from Micromeritics. The method is well known to the skilled person and defined in ISO 9277:2010. Samples are conditioned at 150° C. under vacuum for a period of 60 min prior to measurement.

In one embodiment, the magnesium ion-containing material contains up to 25 000 ppm $Ca^{2+}$ ions. For example, the magnesium ion-containing material contains up to 20 000 ppm, more preferably up to 15 000 ppm and most preferably up to 5 000 ppm $Ca^{2+}$ ions.

According to the present invention, the surface-treated magnesium ion-containing material is obtained by treating the surface of the magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate-, and/or aluminate-group containing compound, and a corresponding salt thereof.

Accordingly, it should be noted that the surface-treated magnesium ion-containing material is obtained by treating the surface of the magnesium ion-containing material with one compound. Alternatively, the surface-treated magnesium ion-containing material is obtained by treating the surface of the magnesium ion-containing material with two or more compounds. For example, the surface-treated magnesium ion-containing material is obtained by treating the surface of the magnesium ion-containing material with two or three or four compounds, like two compounds.

In one embodiment of the present invention, the surface-treated magnesium ion-containing material is obtained by treating the surface of the magnesium ion-containing material with two compounds.

According to one embodiment, the surface-treated magnesium ion-containing material is obtained by treating the surface of the magnesium ion-containing material with phosphoric acid.

In one embodiment, the surface-treated magnesium ion-containing material is obtained by treating the surface of the magnesium ion-containing material with a salt of phosphoric acid, e.g. an alkali metal salt of phosphoric acid. For example, the alkali metal salt of phosphoric acid is sodium phosphate or potassium phosphate, preferably sodium phosphate.

Additionally or alternatively, the surface-treated magnesium ion-containing material is obtained by treating the surface of the magnesium ion-containing material with a polyphosphate.

It is to be noted that a "polyphosphate" in the meaning of the present invention refers to the condensation products of the salts of ortho phosphoric acid. The polyphosphate is typically of the formula $M_{(n+2)}P_nO_{(3n+1)}$, wherein n is an integer of ≥2, preferably in the range from 2 to 30, more preferably from 4 to 20, most preferably from 10 to 15; and M is selected from a proton, an alkali metal ion and mixtures thereof, preferably $H^+$, $Na^+$ and/or $K^+$, more preferably $H^+$ and/or Nat. Thus, the polyphosphate is preferably a linear or branched polyphosphate. The polyphosphate is preferably selected from diphosphates, triphosphates, tetraphosphates and higher phosphate polymers. The polyphosphate is in the form of a salt and preferably comprises an alkali metal ion, more preferably sodium or potassium ions. Additionally or alternatively, the polyphosphate is a hydrate salt of the polyphosphate.

Additionally or alternatively, the polyphosphate is a cyclic polyphosphate (also called polymeric metaphosphate) of the general formula $M_nP_nO_{3n}$, wherein n is an integer of ≥2, preferably in the range from 2 to 20, more preferably from 2 to 10, even more preferably from 2 to 8, most preferably n is 3, 4 or 6, e.g. n is 6; and M is selected from a proton, an alkali metal ion and mixtures thereof, preferably $H^+$, $Na^+$ and/or $K^+$, more preferably $H^+$ and/or Nat.

Thus, the polyphosphate is preferably monosodium diphosphate (anhydrous) ($NaH_3P_2O_7$), disodium diphosphate (anhydrous) ($Na_2H_2P_2O_7$), disodium diphosphate (hexahydrate) ($Na_2H_2P_2O_7$ $(H_2O)_6$), trisodium diphosphate (anhydrous) ($Na_3HP_2O_7$), trisodium diphosphate (monohydrate) ($Na_3HP_2O_7$ $(H_2O)$)), trisodium diphosphate (nonahydrate) ($Na_3HP_2O_7$ $(H_2O)_9$), tetrasodium diphosphate (anhydrous) ($Na_4P_2O_7$), tetrasodium diphosphate (decahydrate) ($Na_4P_2O_7(H_2O)_{10}$), or sodium polyphosphate, wherein n in the formula $M_{(n+2)}P_nO_{(3n+1)}$ is from 4 to 20 and preferably from 10 to 15.

Additionally or alternatively, the surface-treated magnesium ion-containing material is obtained by treating the surface of the magnesium ion-containing material with a carboxylic acid containing up to six carbon atoms.

The carboxylic acid containing up to six carbon atoms is preferably an aliphatic carboxylic acid and may be selected from one or more linear chain, branched chain, saturated, unsaturated and/or alicyclic carboxylic acids. Preferably, the carboxylic acid containing up to six carbon atoms is a monocarboxylic acid, i.e. the carboxylic acid containing up to six carbon atoms is characterized in that a single carboxyl group is present. Said carboxyl group is placed at the end of the carbon skeleton.

In one embodiment of the present invention, the carboxylic acid containing up to six carbon atoms is preferably selected from the group consisting of carbonic acid, formic acid, acetic acid, propanoic acid, butanoic acid, pentanoic acid, hexanoic acid and mixtures thereof. More preferably, the carboxylic acid containing up to six carbon atoms is selected from the group consisting of propanoic acid, butanoic acid, pentanoic acid, hexanoic acid and mixtures thereof.

For example, the carboxylic acid containing up to six carbon atoms is selected from the group consisting of butanoic acid, pentanoic acid, hexanoic acid and mixtures thereof. Preferably, the carboxylic acid containing up to six carbon atoms is selected from the group consisting of pentanoic acid, hexanoic acid and mixtures thereof.

In one embodiment, the carboxylic acid containing up to six carbon atoms is pentanoic acid.

In one embodiment, the surface-treated magnesium ion-containing material is obtained by treating the surface of the magnesium ion-containing material with a salt of the carboxylic acid containing up to six carbon atoms, e.g. an alkali metal salt of the carboxylic acid containing up to six carbon atoms. For example, the alkali metal salt of the carboxylic acid containing up to six carbon atoms is sodium pentanoate or potassium pentanoate, preferably sodium pentanoate.

Additionally or alternatively, the surface-treated magnesium ion-containing material is obtained by treating the surface of the magnesium ion-containing material with a di- and/or tri-carboxylic acid containing up to six carbon atoms where the carboxylic acid groups are linked by a chain of 0-4 intermittent carbon atoms.

The dicarboxylic acid containing up to six carbon atoms is characterized in that two carboxyl groups are present. Said carboxyl groups are preferably placed at each end of the carbon skeleton with the proviso that the carboxylic acid groups are linked by a chain of 0-4 intermittent carbon atoms.

In one embodiment of the present invention, the dicarboxylic acid containing up to six carbon atoms is preferably selected from the group consisting of oxalic acid, malonic acid, succinic acid, glutaric acid, adipic acid, tartaric acid, fumaric acid and mixtures thereof. More preferably, the dicarboxylic acid containing up to six carbon atoms is selected from the group consisting of oxalic acid, malonic acid, tartaric acid, fumaric acid and mixtures thereof.

For example, the dicarboxylic acid containing up to six carbon atoms is preferably selected from the group consisting of oxalic acid, and/or tartaric acid. Most preferably, the dicarboxylic acid containing up to six carbon atoms is oxalic acid.

In one embodiment, the surface-treated magnesium ion-containing material is obtained by treating the surface of the magnesium ion-containing material with a salt of the dicarboxylic acid containing up to six carbon atoms, e.g. an alkali metal salt of the dicarboxylic acid containing up to six carbon atoms. For example, the alkali metal salt of the dicarboxylic acid containing up to six carbon atoms is sodium oxalate, sodium tartrate, potassium oxalate or potassium tartrate, preferably sodium oxalate or sodium tartrate, more preferably sodium oxalate. It is appreciated that the salt of the dicarboxylic acid containing up to six carbon atoms can be a monobasic or dibasic salt of the dicarboxylic acid. For example, the salt of the dicarboxylic acid containing up to six carbon atoms can be a monobasic or dibasic oxalate, such as monobasic or dibasic sodium oxalate.

The tricarboxylic acid containing up to six carbon atoms is characterized in that three carboxyl groups are present. Two carboxyl groups are placed at each end of the carbon skeleton with the proviso that the two carboxylic acid groups are linked by a chain of 0-4 intermittent carbon atoms.

In one embodiment of the present invention, the tricarboxylic acid containing up to six carbon atoms is preferably selected from the group consisting of citric acid, isocitric acid, aconitic acid and mixtures thereof. More preferably, the tricarboxylic acid containing up to six carbon atoms is selected from citric acid and/or isocitric acid.

Most preferably, the tricarboxylic acid containing up to six carbon atoms is citric acid.

In one embodiment, the surface-treated magnesium ion-containing material is obtained by treating the surface of the magnesium ion-containing material with a salt of the tricarboxylic acid containing up to six carbon atoms, e.g. an alkali metal salt of the tricarboxylic acid containing up to six carbon atoms. For example, the alkali metal salt of the tricarboxylic acid containing up to six carbon atoms is sodium citrate or potassium citrate, preferably sodium citrate. It is appreciated that the salt of the tricarboxylic acid containing up to six carbon atoms can be a monobasic or dibasic or tribasic salt of the tricarboxylic acid. For example, the salt of the tricarboxylic acid containing up to six carbon atoms can be a monobasic or dibasic or tribasic citrate, such as monobasic or dibasic or tribasic sodium citrate.

Additionally or alternatively, the surface-treated magnesium ion-containing material is obtained by treating the surface of the magnesium ion-containing material with a water-insoluble polymer.

Preferably, the water-insoluble polymer is selected from polyvinyl ether, polypropylene glycol, carboxymethyl cellulose and mixtures thereof. Such polymers are well known in the art.

In one embodiment, the water-insoluble polymer has a melting temperature Tm between 25-150° C.

The water-insoluble polymer preferably has a solubility in water at 23° C. (+2° C.) of less than or equal to 10 mg/L.

In one embodiment, the surface-treated magnesium ion-containing material is obtained by treating the surface of the magnesium ion-containing material with a salt of the water-insoluble polymer, e.g. an alkali metal salt of the water-insoluble polymer. For example, the alkali metal salt of the water-insoluble polymer atoms is sodium carboxymethyl cellulose or potassium carboxymethyl cellulose, preferably sodium carboxymethyl cellulose.

Additionally or alternatively, the surface-treated magnesium ion-containing material is obtained by treating the surface of the magnesium ion-containing material with a water-insoluble wax.

Preferably, the water-insoluble wax is paraffin wax or lanolin. It is appreciated that paraffin wax consists of a mixture of hydrocarbon molecules containing between twenty and forty carbon atoms. Lanolin is typically composed predominantly of long-chain waxy esters and the remainder being lanolin alcohols, lanolin acids and lanolin hydrocarbons. Such waxes are well known in the art.

In one embodiment, the water-insoluble wax has a melting temperature Tm between 25-150° C.

The water-insoluble wax preferably has a solubility in water at 23° C. (+2° C.) of less than or equal to 10 mg/L.

In one embodiment, the surface-treated magnesium ion-containing material is obtained by treating the surface of the magnesium ion-containing material with a salt of the water-insoluble wax, e.g. an alkali metal salt of the water-insoluble wax preferably a sodium salt of the water-insoluble wax.

In one embodiment, the surface-treated magnesium ion-containing material is obtained by treating the surface of the magnesium ion-containing material with a silicate-, and/or aluminate-group containing compound.

For example, the surface-treated magnesium ion-containing material is obtained by treating the surface of the magnesium ion-containing material with a silicate- or aluminate-group containing compound. Alternatively, the surface-treated magnesium ion-containing material is obtained by treating the surface of the magnesium ion-containing material with a silicate- and aluminate-group containing compound.

It is appreciated that the silicate-, and/or aluminate-group containing compound is preferably a silicate- or aluminate-group containing compound.

Preferably, the silicate-, and/or aluminate-group containing compound is selected from the group comprising alkali metal silicates, alkali metal aluminates, silicon alkoxides and aluminium alkoxides. More preferably, the silicate-, and/or aluminate-group containing compound is selected from the group comprising sodium silicate, potassium silicate, sodium aluminate, potassium aluminate, tetramethyl orthosilicate, tetraethyl orthosilicate, aluminium methoxide, aluminium ethoxide, aluminium isopropoxide, and mixtures thereof. Most preferably, the silicate-, and/or aluminate-group containing compound is selected from the group comprising sodium silicate, tetraethyl orthosilicate, and aluminium isopropoxide. For example, the silicate-group containing compound is sodium silicate, preferably in the form of an aqueous solution which is also called “water glass” or “sodium water glass”.

Preferably, the surface-treated magnesium ion-containing material is obtained by treating the surface of the magnesium ion-containing material with phosphoric acid or an alkali metal salt of phosphoric acid, such as sodium phosphate, more preferably an alkali metal salt of phosphoric acid, such as sodium phosphate. Alternatively, the surface-treated magnesium ion-containing material is obtained by treating the surface of the magnesium ion-containing material with a polyphosphate, such as tetrasodium diphosphate (anhydrous) ($Na_4P_2O_7$) or sodium polyphosphate. Alternatively, the surface-treated magnesium ion-containing material is obtained by treating the surface of the magnesium ion-containing material with citric acid or an alkali metal salt of citric acid, such as sodium citrate, more preferably an alkali metal salt of citric acid, such as sodium citrate.

In view of the above, the surface of the magnesium ion-containing material preferably comprises one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, and a corresponding salt thereof and/or reaction products thereof.

The term “reaction products” in the meaning of the present invention refers to products obtained by contacting the surface of the magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof. Said reaction products are formed between the applied one or more compound(s) and reactive molecules located at the surface of the magnesium ion-containing material.

In one embodiment, the surface-treated magnesium ion-containing material is preferably obtained by treating the surface of dolomite ($CaMg(CO_3)_2$), e.g. naturally occurring dolomite ($CaMg(CO_3)_2$), with phosphoric acid.

In an alternative embodiment, the surface-treated magnesium ion-containing material is preferably obtained by treating the surface of dolomite ($CaMg(CO_3)_2$), e.g. naturally occurring dolomite ($CaMg(CO_3)_2$), with a polyphosphate, preferably sodium polyphosphate. More preferably sodium polyphosphate, wherein n in the formula $M_{(n+2)}P_nO_{(3n+1)}$ is an integer of ≥2, preferably in the range from 2 to 30, more preferably from 4 to 20, most preferably from 10 to 15.

In an alternative embodiment, the surface-treated magnesium ion-containing material is preferably obtained by treating the surface of dolomite ($CaMg(CO_3)_2$), e.g. naturally occurring dolomite ($CaMg(CO_3)_2$), with a di- or tri-carboxylic acid, preferably oxalic acid, tartaric acid, or citric acid. For example, the surface-treated magnesium ion-containing material is obtained by treating the surface of dolomite ($CaMg(CO_3)_2$), e.g. naturally occurring dolomite ($CaMg(CO_3)_2$), with a salt of the di- or tri-carboxylic acid, preferably sodium oxalate, sodium tartrate or sodium citrate. Preferably, the salt of the di- or tri-carboxylic acid, e.g. the sodium oxalate, sodium tartrate or sodium citrate, is a monobasic salt. It is appreciated that the surface-treated magnesium ion-containing material is preferably obtained by treating the surface of the magnesium ion-containing material with the one or more compound(s) in an amount from 0.1 to 25 wt.-%, based on the total dry weight of the magnesium ion-containing material. For example, the surface-treated magnesium ion-containing material is preferably obtained by treating the surface of the magnesium ion-containing material with the one or more compound(s) in an amount from 0.1 to 20 wt.-%, based on the total dry weight of the magnesium ion-containing material. Preferably, the surface-treated magnesium ion-containing material is obtained by treating the surface of the magnesium ion-containing material with the one or more compound(s) in an amount from 0.3 to 10 wt.-%, based on the total dry weight of the magnesium ion-containing material. Even more preferably, the surface-treated magnesium ion-containing material is obtained by treating the surface of the magnesium ion-containing material with the one or more compound(s) in an amount from 0.5 to 5 wt.-%, based on the total dry weight of the magnesium ion-containing material.

In general, the surface-treated magnesium ion-containing material can be prepared by any known method suitable for obtaining a treatment layer of one or more compound(s) on the surface of filler materials such as magnesium ion-containing material.

For example, the surface-treated magnesium ion-containing material is prepared in a dry method, e.g. by applying the one or more compound(s) onto the surface of the magnesium ion-containing material without using solvents. If the one or more compound(s) are in a solid state, the one or more compound(s) may be heated in order to provide them in a liquid state for ensuring an essentially even distribution of the one or more compound(s) on the surface of the magnesium ion-containing material.

Alternatively, the surface-treated magnesium ion-containing material is prepared in a wet method, e.g. by dissolving the one or more compound(s) in a solvent and applying the mixture onto the surface of the magnesium ion-containing material. Optionally the mixture comprising the solvent and the one or more compound(s) may be heated. If the one or more compound(s) are dissolved in a solvent, the solvent is preferably water or an organic solvent, preferably selected from methanol, acetone, isopropyl alcohol, 1,3-butylene glycol, ethyl acetate, glycerol, hexane, methylene chloride and ethanol.

In general, the step of applying the one or more compound(s) on the surface of the magnesium ion-containing material may be carried out by any method suitable for achieving an essentially even distribution of the one or more compound(s) on the surface of the magnesium ion-containing material. Thus, the one or more compound(s) and the magnesium ion-containing material should be agitated or shaken to facilitate and accelerate the preparation of the surface-treated magnesium ion-containing material, e.g. by using a mixing device, spray coater or encapsulation processes. If a solvent is use, the obtained surface-treated magnesium ion-containing material may be dried to remove the volatile components, preferably under vacuum.

In the dry and wet method, the step of applying the one or more compound(s) on the surface of the magnesium ion-containing material may be carried out in a single step or in at least two steps. According to one embodiment of the present invention, the surface-treated magnesium ion-containing material is thus prepared by means of one or more of the following methods:

(i) dry treatment, i.e. treating the surface of the magnesium ion-containing material with the one or more compound(s) which is/are in neat form, preferably in a mixing device or by using a spray coater;

(ii) wet treatment, i.e. treating the surface of the magnesium ion-containing material with the one or more compound(s) which is/are dissolved in a solvent, optionally under heating, preferably in a mixing device or by using a spray coater; or (iii) melt dry treatment, i.e. treating the surface of the magnesium ion-containing material with a melt of the one or more compound(s) which is/are in neat form in a heated mixer (e.g. a fluid bed mixer).

In general, the surface-treated magnesium ion-containing material obtained is preferably in form of particles having a volume median grain diameter ($d_{50}$) of >150 nm, preferably from 150 nm to 100 μm, more preferably from 0.2 to 50 μm, even more preferably from 0.3 to 40 μm, and most preferably from 0.4 to 30 μm, as determined by laser diffraction. Alternatively, the surface-treated magnesium ion-containing material obtained is preferably in form of particles having a volume median grain diameter ($d_{50}$) of ≥150 nm, preferably from 150 nm to 20 μm, more preferably from 0.2 to 15 μm, even more preferably from 0.5 to 10 μm, and most preferably from 1 to 5 μm, as determined by laser diffraction. According to a further embodiment of the present invention, the surface-treated magnesium ion-containing material is in form of particles having a volume determined top cut particle size ($d_{98}$) of equal to or less than 120 μm, preferably from 1 to 100 μm, more preferably from 1 to 90 μm, and most preferably from 1.5 to 80 μm, as determined by laser diffraction.

For example, the surface-treated magnesium ion-containing material is in form of particles having a volume determined top cut particle size ($d_{98}$) of equal to or less than 30 μm, preferably from 2 to 30 μm, more preferably from 5 to 20 μm, and most preferably from 8 to 18 μm, as determined by laser diffraction.

However, it is possible that the surface-treated magnesium ion-containing material forms artefacts of incomplete deagglomerates in lab scale, such that the volume median grain diameter ($d_{50}$) as well as the volume determined top cut particle size ($d_{98}$) of the surface-treated magnesium ion-containing material obtained in lab scale may be higher than that obtained in full scale.

Thus, the surface-treated magnesium ion-containing material is in form of particles preferably having a) a volume median grain diameter ($d_{50}$) of ≥150 nm, preferably from 150 nm to 100 μm, more preferably from 0.2 to 50 μm, even more preferably from 0.3 to 40 μm, and most preferably from 0.4 to 30 μm, as determined by laser diffraction, and b) a volume determined top cut particle size ($d_{98}$) of equal to or less than 120 μm, preferably from 1 to 100 μm, more preferably from 1 to 90 μm, and most preferably from 1.5 to 80 μm, as determined by laser diffraction.

In one embodiment, the surface-treated magnesium ion-containing material is in form of particles having a volume median grain diameter ($d_{50}$) in the range from 0.4 to 30 μm, as determined by laser diffraction, and a volume determined top cut particle size ($d_{98}$) in the range from 1.5 to 80 μm, as determined by laser diffraction.

For example, the surface-treated magnesium ion-containing material is obtained by treating the surface of anhydrous magnesium carbonate or magnesite ($MgCO_3$) or dolomite ($CaMg(CO_3)_2$) or hydromagnesite ($Mg_5(CO_3)_4(OH)_2 \cdot 4H_2O$) or brucite ($Mg(OH)_2$), e.g. synthetic hydromagnesite ($Mg_5(CO_3)_4(OH)_2 \cdot 4H_2O$) or brucite ($Mg(OH)_2$) or naturally occurring anhydrous magnesium carbonate or magnesite ($MgCO_3$) or dolomite ($CaMg(CO_3)_2$), with phosphoric acid, sodium phosphate, citric acid, sodium citrate, pentanoic acid, and mixtures thereof and has a volume median grain diameter ($d_{50}$) in the range from 0.4 to 30 μm, as determined by laser diffraction, and a volume determined top cut particle size ($d_{98}$) in the range from 1.5 to 80 μm, as determined by laser diffraction.

In one embodiment, the surface-treated magnesium ion-containing material is obtained by treating the surface of dolomite ($CaMg(CO_3)_2$), e.g. naturally occurring dolomite ($CaMg(CO_3)_2$), with phosphoric acid and has a volume median grain diameter ($d_{50}$) in the range from 0.4 to 30 μm, as determined by laser diffraction, and a volume determined top cut particle size ($d_{98}$) in the range from 1.5 to 80 μm, as determined by laser diffraction.

In an alternative embodiment, the surface-treated magnesium ion-containing material is preferably obtained by treating the surface of dolomite ($CaMg(CO_3)_2$), e.g. naturally occurring dolomite ($CaMg(CO_3)_2$), with a polyphosphate, preferably tetrasodium diphosphate (anhydrous) ($Na_4P_2O_7$) or sodium polyphosphate, and has a volume median grain diameter ($d_{50}$) in the range from 0.4 to 30 μm as determined by laser diffraction, and a volume determined top cut particle size ($d_{98}$) in the range from 1.5 to 80 μm, as determined by laser diffraction.

In an alternative embodiment, the surface-treated magnesium ion-containing material is preferably obtained by treating the surface of dolomite ($CaMg(CO_3)_2$), e.g. naturally occurring dolomite ($CaMg(CO_3)_2$), with a di- or tri-carboxylic acid, preferably oxalic acid, tartaric acid, or citric acid and has a volume median grain diameter ($d_{50}$) in the range from 0.4 to 30 μm, as determined by laser diffraction, and a volume determined top cut particle size ($d_{98}$) in the range from 1.5 to 80 μm, as determined by laser diffraction. For example, the surface-treated magnesium ion-containing material is obtained by treating the surface of dolomite ($CaMg(CO_3)_2$), e.g. naturally occurring dolomite ($CaMg(CO_3)_2$), with a salt of the di- or tri-carboxylic acid, preferably sodium oxalate, sodium tartrate or sodium citrate and has a volume median grain diameter ($d_{50}$) in the range from 0.4 to 30 μm, as determined by laser diffraction, and a volume determined top cut particle size ($d_{98}$) in the range from 1.5 to 80 μm, as determined by laser diffraction.

In an alternative embodiment, the surface-treated magnesium ion-containing material is preferably obtained by treating the surface of dolomite ($CaMg(CO_3)_2$), e.g. naturally occurring dolomite ($CaMg(CO_3)_2$), with a silicate- and/or aluminate-group containing compound, preferably selected from the group comprising alkali metal silicates, alkali metal aluminates, silicon alkoxides and aluminium alkoxides, more preferably from sodium silicate, potassium silicate, sodium aluminate, potassium aluminate, tetramethyl orthosilicate, tetraethyl orthosilicate, aluminium methoxide, aluminium ethoxide, aluminium isopropoxide, and mixtures thereof, and most preferably from sodium silicate, tetraethyl orthosilicate, and aluminium isopropoxide, and has a volume median grain diameter ($d_{50}$) in the range from 0.4 to 30 μm, as determined by laser diffraction, and a volume determined top cut particle size ($d_{98}$) in the range from 1.5 to 80 μm, as determined by laser diffraction.

It is appreciated that the ratio of volume determined top cut particle size ($d_{98}$) to volume median grain diameter ($d_{50}$) [$d_{98}$:$d_{50}$] for the surface-treated magnesium ion-containing material is preferably below 50, more preferably between 2 and 30, and most preferably between 2.5 and 10. The foregoing applies to a properly deagglomerated material, i.e. a material not forming artefacts.

Additionally or alternatively, the surface-treated magnesium ion-containing material has a whiteness determined as CIELAB L* of >90%, preferably >95%, more preferably >98% and most preferably >98.5% and measured dry according to EN ISO 11664 4:2010.

In one embodiment, the surface-treated magnesium ion-containing material is in form of particles having a BET specific surface area in the range from 2 to 200 $m^2/g$, preferably from 3 to 100 $m^2/g$, and most preferably from 4 to 75 $m^2/g$, measured using nitrogen and the BET method according to ISO 9277:2010.

Oral Care Composition

According to the present invention, an oral care composition is provided. The oral care composition comprises the surface-treated magnesium ion-containing material according to the present invention, i.e. the surface-treated magnesium ion-containing material obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

With regard to the definition of the surface-treated magnesium ion-containing material and preferred embodiments thereof, reference is made to the statements provided above when discussing the technical details of the surface-treated magnesium ion-containing material of the present invention.

Additionally or alternatively, the oral care composition comprises a surface-treated calcium ion-containing material obtained by treating the surface of a calcium ion-containing material with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

According to another embodiment of the present invention, an oral care composition is provided comprising a surface-treated magnesium ion-containing material obtained by treating the surface of a magnesium ion-containing material with one or more compound(s) selected from the group consisting of phosphoric acid, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof and a surface-treated calcium ion-containing material obtained by treating the surface of a calcium ion-containing material with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

It is appreciated that the term "calcium ion-containing material" refers to a material that comprises at least 55 wt.-% of a calcium compound, e.g. at least 58 wt.-%, preferably between 58 and 100 wt.-%, more preferably between 85 and 100 wt.-% and most preferably between 90 and 99.95 wt.-%, based on the total dry weight of the material. Thus, it is to be noted that the calcium ion-containing material may further comprise impurities typically associated with the type of material used. For example, the calcium ion-containing material may further comprise impurities such as magnesium ion-containing materials like magnesium hydroxide, magnesium carbonate and mixtures thereof. However, such impurities are present in amounts of less than 45 wt.-%, preferably less than 42 wt.-%, more preferably from 0 to 42 wt. %, even more preferably from 0 to 15 wt.-% and most preferably from 0.05 to 10 wt.-%, based on the total dry weight of the material.

The calcium ion-containing material can be a naturally occurring or synthetic calcium ion-containing material.

Preferably, the calcium ion-containing material is naturally occurring or synthetic calcium carbonate. That is to say, the calcium ion-containing material is preferably selected from ground calcium carbonate, precipitated calcium carbonate, surface-reacted calcium carbonate, dolomite, dolocarbonate and mixtures thereof.

According to one embodiment, the calcium ion-containing material is ground calcium carbonate and/or precipitated calcium carbonate. Preferably, the calcium ion-containing material is ground calcium carbonate or precipitated calcium carbonate, more preferably ground calcium carbonate.

"Ground calcium carbonate" (GCC) in the meaning of the present invention is a calcium carbonate obtained from natural sources, such as limestone, marble, dolomite, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form.

For the purpose of the present invention, a "surface-reacted calcium carbonate" is a material comprising calcium carbonate and an insoluble, at least partially crystalline, non-carbonate calcium salt, preferably, extending from the surface of at least part of the calcium carbonate. The calcium ions forming said at least partially crystalline non-carbonate calcium salt originate largely from the starting calcium carbonate material that also serves to form the surface-reacted calcium carbonate core. Such salts may include OH anions and/or crystal water.

In one embodiment, the calcium ion-containing material comprises ground calcium carbonate, precipitated calcium carbonate, surface-reacted calcium carbonate and mixtures thereof in an amount of at least 80 wt.-%, more preferably at least 85 wt.-%, even more preferably between 85 and 100 wt.-%, and most preferably between 90 and 99.95 wt.-%, based on the total dry weight of the material.

Preferably, the calcium ion-containing material comprises ground calcium carbonate and/or precipitated calcium carbonate, more preferably ground calcium carbonate, in an amount of at least 80 wt.-%, more preferably at least 85 wt.-%, even more preferably between 85 and 100 wt.-%, and most preferably between 90 and 99.95 wt.-%, based on the total dry weight of the material.

According to one embodiment of the present invention, the calcium ion-containing material is in form of particles having a volume median grain diameter ($d_{50}$) of >150 nm, preferably from 150 nm to 20 μm, more preferably from 0.2 to 15 μm, even more preferably from 0.5 to 10 μm, and most preferably from 1 to 8 μm, as determined by laser diffraction. According to a further embodiment of the present invention, the calcium ion-containing material is in form of particles having a volume determined top cut particle size ($d_{98}$) of equal to or less than 30 μm, preferably from 2 to 30 μm, more preferably from 5 to 20 μm, and most preferably from 8 to 18 μm, as determined by laser diffraction.

Throughout the present document, the "particle size" of a calcium ion-containing material is described by its distribution of particle sizes on a volume base. Volume determined median grain diameter $d_{50}$ (or $d_{50}$(vol)) and the volume determined top cut particle size $d_{98}$ (or $d_{98}$(vol)) was evaluated using a Malvern Mastersizer 3000 Laser Diffraction System (Malvern Instruments Plc., Great Britain) equipped with a Hydro LV system. The $d_{50}$(vol) or $d_{98}$(vol) value indicates a diameter value such that 50% or 98% by volume, respectively, of the particles have a diameter of less than this value. The powders were suspended in 0.1 wt.-% $Na_4O_7P_2$ solution. 10 mL of 0.1 wt.-% $Na_4O_7P_2$ was added to the Hydro LV tank, then the sample slurry was introduced until an obscuration between 10-20% was achieved. Measurements were conducted with red and blue light for 10 s each. For the analysis of the raw data, the models for non-spherical particle sizes using Mie theory was utilized, and a particle refractive index of 1.57, a density of 2.70 g/cm$^3$, and an absorption index of 0.005 was assumed. The methods and instruments are known to the skilled person and are commonly used to determine particle size distributions of fillers and pigments. Furthermore, the particle sizes described above for the magnesium ion-containing material as well as the surface-treated magnesium ion-containing material are also applicable for the surface-reacted calcium carbonate as well as the corresponding surface-treated surface-reacted calcium carbonate.

Thus, the calcium ion-containing material is in form of particles preferably having a) a volume median grain diameter ($d_{50}$) of ≥150 nm, preferably from 150 nm to 20 μm, more preferably from 0.2 to 15 μm, even more preferably from 0.5 to 10 μm, and most preferably from 1 to 8 μm, as determined by laser diffraction, and b) a volume determined top cut particle size ($d_{98}$) of equal to or less than 30 μm, preferably from 2 to 30 μm, more preferably from 5 to 20 μm, and most preferably from 8 to 18 μm, as determined by laser diffraction.

In one embodiment, the calcium ion-containing material is in form of particles having a volume median grain diameter ($d_{50}$) in the range from >150 nm, preferably from 150 nm to 20 μm, more preferably from 0.2 to 15 μm, even more preferably from 0.5 to 10 μm, and most preferably from 1 to 8 μm, as determined by laser diffraction, and a volume determined top cut particle size ($d_{98}$) in the range from 8 to 18 μm, as determined by laser diffraction.

For example, the calcium ion-containing material comprises ground calcium carbonate and/or precipitated calcium carbonate, more preferably ground calcium carbonate, and has a volume median grain diameter ($d_{50}$) in the range from 1 to 8 μm, as by laser diffraction, and a volume determined top cut particle size ($d_{98}$) in the range from 8 to 18 μm, as determined by laser diffraction. In one embodiment, the calcium ion-containing material comprises ground calcium carbonate and/or precipitated calcium carbonate, more preferably ground calcium carbonate, in an amount of at least 80 wt.-%, more preferably at least 85 wt.-%, even more preferably between 85 and 100 wt.-%, and most preferably between 90 and 99.95 wt.-%, based on the total dry weight of the material and has a volume median grain diameter ($d_{50}$) in the range from 1 to 8 μm, as determined by laser diffraction, and a volume determined top cut particle size ($d_{98}$) in the range from 8 to 18 μm, as determined by laser diffraction.

If the surface-treated magnesium ion-containing material is used as opacifying agent and/or whitening pigment, the surface-treated calcium ion-containing material is preferably obtained by treating the surface of ground calcium carbonate and/or precipitated calcium carbonate with one or more compound(s) selected from the group consisting of, a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

If the surface-treated magnesium ion-containing material is used for improving the availability of fluoride ions in oral care compositions, the surface-treated calcium ion-containing material is preferably obtained by treating the surface of surface-reacted calcium carbonate with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

Additionally or alternatively, the calcium ion-containing material has a whiteness determined as CIELAB L* of >90%, preferably >95%, more preferably >98% and most preferably >98.5% and measured dry according to EN ISO 11664 4:2010.

In one embodiment, the calcium ion-containing material is in form of particles having a BET specific surface area in the range from 2 to 200 $m^2/g$, preferably from 10 to 100 $m^2/g$, and most preferably from 12 to 75 $m^2/g$, measured using nitrogen and the BET method according to ISO 9277:2010.

In one embodiment, the calcium ion-containing material contains up to 25 000 ppm $Mg^{2+}$ ions. For example, the calcium ion-containing material contains up to 20 000 ppm, more preferably up to 15 000 ppm and most preferably up to 5 000 ppm $Mg^{2+}$ ions.

According to the present invention, the surface-treated calcium ion-containing material is obtained by treating the surface of the calcium ion-containing material with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof.

Accordingly, it should be noted that the surface-treated calcium ion-containing material is obtained by treating the surface of the calcium ion-containing material with one compound. Alternatively, the surface-treated calcium ion-containing material is obtained by treating the surface of the calcium ion-containing material with two or more compounds. For example, the surface-treated calcium ion-containing material is obtained by treating the surface of the calcium ion-containing material with two or three or four compounds, like two compounds.

In one embodiment of the present invention, the surface-treated calcium ion-containing material is obtained by treating the surface of the calcium ion-containing material with two compounds. According to one embodiment, the surface-treated calcium ion-containing material is obtained by treating the surface of the calcium ion-containing material with a polyphosphate.

A "polyphosphate" in the meaning of the present invention refers to the condensation products of the salts of ortho phosphoric acid. The polyphosphate is typically of the formula $M_{(n+2)}P_nO_{(3n+1)}$, wherein n is an integer of >2, preferably in the range from 2 to 30, more preferably from 4 to 20, most preferably from 10 to 15; and M is selected from a proton, an alkali metal ion and mixtures thereof, preferably $H^+$, $Na^+$ and/or $K^+$, more preferably $H^+$ and/or Nat. Thus, the polyphosphate is preferably a linear or branched polyphosphate. The polyphosphate is preferably selected from diphosphates, triphosphates, tetraphosphates and higher phosphate polymers. The polyphosphate is in the form of a salt and preferably comprises an alkali metal ion, more preferably sodium or potassium ions. Additionally or alternatively, the polyphosphate is a hydrate salt of the polyphosphate.

Additionally or alternatively, the polyphosphate is a cyclic polyphosphate (also called polymeric metaphosphate) of the general formula $M_nP_nO_3n$, wherein n is an integer of ≥2, preferably in the range from 2 to 20, more preferably from 2 to 10, even more preferably from 2 to 8, most preferably n is 3, 4 or 6, e.g. n is 6; and M is selected from a proton, an alkali metal ion and mixtures thereof, preferably $H^+$, $Na^+$ and/or $K^+$, more preferably $H^+$ and/or $Na^+$.

Thus, the polyphosphate is preferably monosodium diphosphate (anhydrous) ($NaH_3P_2O_7$), disodium diphosphate (anhydrous) ($Na_2H_2P_2O_7$), disodium diphosphate (hexahydrate) ($Na_2H_2P_2O_7$ $(H_2O)_6$), trisodium diphosphate (anhydrous) ($Na_3HP_2O_7$), trisodium diphosphate (monohydrate) ($Na_3HP_2O_7$ $(H_2O)$), trisodium diphosphate (nonahydrate) ($Na_3HP_2O_7$ $(H_2O)_9$), tetrasodium diphosphate (anhydrous) ($Na_4P_2O_7$), tetrasodium diphosphate (decahydrate) ($Na_4P_2O_7$ $(H_2O)_{10}$), or sodium polyphosphate, wherein n in the formula $M_{(n+2)}P_nO_{(3n+1)}$ is from 4 to 20, and preferably from 10 to 15.

According to one embodiment, the surface-treated calcium ion-containing material is obtained by treating the surface of the calcium ion-containing material with a carboxylic acid containing up to six carbon atoms.

The carboxylic acid containing up to six carbon atoms is preferably an aliphatic carboxylic acid and may be selected from one or more linear chain, branched chain, saturated, unsaturated and/or alicyclic carboxylic acids. Preferably, the carboxylic acid containing up to six carbon atoms is a monocarboxylic acid, i.e. the carboxylic acid containing up to six carbon atoms is characterized in that a single carboxyl group is present. Said carboxyl group is placed at the end of the carbon skeleton.

In one embodiment of the present invention, the carboxylic acid containing up to six carbon atoms is preferably selected from the group consisting of carbonic acid, formic acid, acetic acid, propanoic acid, butanoic acid, pentanoic acid, hexanoic acid and mixtures thereof. More preferably, the carboxylic acid containing up to six carbon atoms is selected from the group consisting of propanoic acid, butanoic acid, pentanoic acid, hexanoic acid and mixtures thereof.

For example, the carboxylic acid containing up to six carbon atoms is selected from the group consisting of butanoic acid, pentanoic acid, hexanoic acid and mixtures thereof. Preferably, the carboxylic acid containing up to six carbon atoms is selected from the group consisting of pentanoic acid, hexanoic acid and mixtures thereof.

In one embodiment, the carboxylic acid containing up to six carbon atoms is pentanoic acid.

In one embodiment, the surface-treated calcium ion-containing material is obtained by treating the surface of the calcium ion-containing material with a salt of the carboxylic acid containing up to six carbon atoms, e.g. an alkali metal salt of the carboxylic acid containing up to six carbon atoms. For example, the alkali metal salt of the carboxylic acid containing up to six carbon atoms is sodium pentanoate or potassium pentanoate, preferably sodium pentanoate.

Additionally or alternatively, the surface-treated calcium ion-containing material is obtained by treating the surface of the calcium ion-containing material with a di-, and/or tri-carboxylic acid containing up to six carbon atoms where the carboxylic acid groups are linked by a chain of 0-4 intermittent carbon atoms.

The dicarboxylic acid containing up to six carbon atoms is characterized in that two carboxyl groups are present. Said carboxyl groups are placed at each end of the carbon skeleton with the proviso that the carboxylic acid groups are linked by a chain of 0-4 intermittent carbon atoms.

In one embodiment of the present invention, the dicarboxylic acid containing up to six carbon atoms is preferably selected from the group consisting of oxalic acid, malonic acid, succinic acid, glutaric acid, adipic acid, tartaric acid, fumaric acid and mixtures thereof. More preferably, the dicarboxylic acid containing up to six carbon atoms is selected from the group consisting of oxalic acid, malonic acid, tartaric acid, fumaric acid and mixtures thereof.

For example, the dicarboxylic acid containing up to six carbon atoms is preferably selected from the group consisting of oxalic acid, and/or tartaric acid. Most preferably, the dicarboxylic acid containing up to six carbon atoms is oxalic acid.

In one embodiment, the surface-treated calcium ion-containing material is obtained by treating the surface of the calcium ion-containing material with a salt of the dicarboxylic acid containing up to six carbon atoms, e.g. an alkali metal salt of the dicarboxylic acid containing up to six carbon atoms. For example, the alkali metal salt of the dicarboxylic acid containing up to six carbon atoms is sodium oxalate, sodium tartrate potassium oxalate or potassium tartrate, preferably sodium oxalate or sodium tartrate, more preferably sodium oxalate.

The tricarboxylic acid containing up to six carbon atoms is characterized in that three carboxyl groups are present. Two carboxyl groups are placed at each end of the carbon skeleton with the proviso that the two carboxylic acid groups are linked by a chain of 0-4 intermittent carbon atoms.

In one embodiment of the present invention, the tricarboxylic acid containing up to six carbon atoms is preferably selected from the group consisting of citric acid, isocitric acid, aconitic acid and mixtures thereof. More preferably, the tricarboxylic acid containing up to six carbon atoms is selected from citric acid and/or isocitric acid.

Most preferably, the tricarboxylic acid containing up to six carbon atoms is citric acid.

In one embodiment, the surface-treated calcium ion-containing material is obtained by treating the surface of the calcium ion-containing material with a salt of the tricarboxylic acid containing up to six carbon atoms, e.g. an alkali metal salt of the tricarboxylic acid containing up to six carbon atoms. For example, the alkali metal salt of the tricarboxylic acid containing up to six carbon atoms is sodium citrate or potassium citrate, preferably sodium citrate.

Additionally or alternatively, the surface-treated calcium ion-containing material is obtained by treating the surface of the calcium ion-containing material with a water-insoluble polymer.

Preferably, the water-insoluble polymer is selected from polyvinyl ether, polypropylene glycol, carboxymethyl cellulose and mixtures thereof. Such polymers are well known in the art.

In one embodiment, the water-insoluble polymer has a melting temperature Tm between 25-150° C.

The water-insoluble polymer preferably has a solubility in water at 23° C. (+2° C.) of less than or equal to 10 mg/L.

In one embodiment, the surface-treated calcium ion-containing material is obtained by treating the surface of the calcium ion-containing material with a salt of the water-insoluble polymer, e.g. an alkali metal salt of the water-insoluble polymer. For example, the alkali metal salt of the water-insoluble polymer atoms is sodium carboxymethyl cellulose or potassium carboxymethyl cellulose, preferably sodium carboxymethyl cellulose.

Additionally or alternatively, the surface-treated calcium ion-containing material is obtained by treating the surface of the calcium ion-containing material with a water-insoluble wax.

Preferably, the water-insoluble wax is paraffin wax or lanolin. It is appreciated that paraffin wax consists of a mixture of hydrocarbon molecules containing between twenty and forty carbon atoms. Lanolin is typically composed predominantly of long-chain waxy esters and the remainder being lanolin alcohols, lanolin acids and lanolin hydrocarbons. Such waxes are well known in the art.

In one embodiment, the water-insoluble wax has a melting temperature Tm between 25-150° C.

The water-insoluble wax preferably has a solubility in water at 23° C. (+2° C.) of less than or equal to 10 mg/L.

In one embodiment, the surface-treated calcium ion-containing material is obtained by treating the surface of the calcium ion-containing material with a salt of the water-insoluble wax, e.g. an alkali metal salt of the water-insoluble wax preferably a sodium salt of the water-insoluble wax.

In one embodiment, the surface-treated calcium ion-containing material is obtained by treating the surface of the calcium ion-containing material with a silicate-, and/or aluminate-group containing compound.

For example, the surface-treated calcium ion-containing material is obtained by treating the surface of the calcium ion-containing material with a silicate- or aluminate-group containing compound. Alternatively, the surface-treated calcium ion-containing material is obtained by treating the surface of the calcium ion-containing material with a silicate- and aluminate-group containing compound.

It is appreciated that the silicate-, and/or aluminate-group containing compound is preferably a silicate- or aluminate-group containing compound.

Preferably, the silicate-, and/or aluminate-group containing compound is selected from the group comprising alkali metal silicates, alkali metal aluminates, silicon alkoxides and aluminium alkoxides. More preferably, the silicate-, and/or aluminate-group containing compound is selected from the group comprising sodium silicate, potassium silicate, sodium aluminate, potassium aluminate, tetramethyl orthosilicate, tetraethyl orthosilicate, aluminium methoxide, aluminium ethoxide, aluminium isopropoxide, and mixtures thereof. Most preferably, the silicate-, and/or aluminate-group containing compound is selected from the group comprising sodium silicate, tetraethyl orthosilicate, and aluminium isopropoxide.

In view of the above, the silicate-group containing compound is selected from the group comprising alkali metal silicates and silicon alkoxides. More preferably, the silicate-group containing compound is selected from the group comprising sodium silicate, potassium silicate, tetramethyl orthosilicate, tetraethyl orthosilicate, and mixtures thereof. Most preferably, the silicate-group containing compound is selected from the group comprising sodium silicate and tetraethyl orthosilicate. For example, the silicate-group containing compound is sodium silicate, preferably in the form of an aqueous solution which is also called “water glass” or “sodium water glass”.

The aluminate-group containing compound is preferably selected from the group comprising alkali metal aluminates and aluminium alkoxides. More preferably, the aluminate-group containing compound is selected from the group comprising sodium aluminate, potassium aluminate, aluminium methoxide, aluminium ethoxide, aluminium isopropoxide, and mixtures thereof. Most preferably, the aluminate-group containing compound is aluminium isopropoxide.

Preferably, the surface-treated calcium ion-containing material is obtained by treating the surface of the calcium ion-containing material with pentanoic acid or an alkali metal salt of pentanoic acid, such as sodium pentanoate, more preferably pentanoic acid. Alternatively, the surface-treated calcium ion-containing material is obtained by treating the surface of the calcium ion-containing material with citric acid or an alkali metal salt of citric acid, such as sodium citrate, more preferably an alkali metal salt of citric acid, such as sodium citrate.

In view of the above, the surface of the calcium ion-containing material preferably comprises one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof and/or reaction products thereof.

The term "reaction products" in the meaning of the present invention refers to products obtained by contacting the surface of the calcium ion-containing material with one or more compound(s) selected from the group consisting of a polyphosphate, a carboxylic acid containing up to six carbon atoms, a di-, and tri-carboxylic acid containing up to six carbon atoms where the carboxylic acid groups are linked by a chain of 0-4 intermittent carbon atoms, a water-insoluble polymer, a water-insoluble wax, a silicate- and/or aluminate-group containing compound, and a corresponding salt thereof. Said reaction products are formed between the applied one or more compound(s) and reactive molecules located at the surface of the calcium ion-containing material.

It is appreciated that the surface-treated calcium ion-containing material is preferably obtained by treating the surface of the calcium ion-containing material with the one or more compound(s) in an amount from 0.1 to 25 wt.-%, based on the total dry weight of the calcium ion-containing material. For example, the surface-treated calcium ion-containing material is preferably obtained by treating the surface of the calcium ion-containing material with the one or more compound(s) in an amount from 0.1 to 20 wt.-%, based on the total dry weight of the calcium ion-containing material. For example, the surface-treated calcium ion-containing material is preferably obtained by treating the surface of the calcium ion-containing material with the one or more compound(s) in an amount from 0.1 to 20 wt.-%, based on the total dry weight of the calcium ion-containing material. Preferably, the surface-treated calcium ion-containing material is obtained by treating the surface of the calcium ion-containing material with the one or more compound(s) in an amount from 0.3 to 10 wt.-%, based on the total dry weight of the calcium ion-containing material. Even more preferably, the surface-treated calcium ion-containing material is obtained by treating the surface of the calcium ion-containing material with the one or more compound(s) in an amount from 0.5 to 5 wt.-%, based on the total dry weight of the calcium ion-containing material.

In general, the surface-treated calcium ion-containing material can be prepared by any known method suitable for obtaining a treatment layer of one or more compound(s) on the surface of filler materials such as calcium ion-containing materials. In particular, reference is made to the statements provided above when discussing the technical details for the preparation of the surface-treated magnesium ion-containing material of the present invention. The same methods can be applied for the preparation of the surface-treated calcium ion-containing material.

The surface-treated calcium ion-containing material obtained is preferably in form of particles having a volume median grain diameter ($d_{50}$) of ≥150 nm, preferably from 150 nm to 200 μm, more preferably from 0.2 to 35 μm, even more preferably from 0.5 to 30 μm, and most preferably from 1 to 25 μm, as determined by laser diffraction. According to a further embodiment of the present invention, the surface-treated calcium ion-containing material is in form of particles having a volume determined top cut particle size ($d_{98}$) of equal to or less than 3000 μm, preferably from 1 to 600 μm, more preferably from 1 to 400 μm, and most preferably from 1.5 to 250 μm, as determined by laser diffraction.

Thus, the surface-treated calcium ion-containing material is in form of particles preferably having c) a volume median grain diameter ($d_{50}$) of ≥150 nm, preferably from 150 nm to 200 μm, more preferably from 0.2 to 35 μm, even more preferably from 0.5 to 30 μm, and most preferably from 1 to 25 μm, as determined by laser diffraction, and d) a volume determined top cut particle size ($d_{98}$) of equal to or less than 3000 μm, preferably from 1 to 600 μm, more preferably from 1 to 400 μm, and most preferably from 1.5 to 250 μm, as determined by laser diffraction.

In one embodiment, the surface-treated calcium ion-containing material is in form of particles having a volume median grain diameter ($d_{50}$) in the range from 1 to 25 μm, as determined by laser diffraction, and a volume determined top cut particle size ($d_{98}$) in the range from 1.5 to 250 μm, as determined by laser diffraction.

For example, the surface-treated calcium ion-containing material is obtained by treating the surface of ground calcium carbonate and/or precipitated calcium carbonate, more preferably ground calcium carbonate, with citric acid, sodium citrate, pentanoic acid, and mixtures thereof and has a volume median grain diameter ($d_{50}$) in the range from 1 to 25 μm, as determined by laser diffraction, and a volume determined top cut particle size ($d_{98}$) in the range from 1.5 to 250 μm, as determined by laser diffraction.

Additionally or alternatively, the surface-treated calcium ion-containing material has a whiteness determined as CIELAB L* of >90%, preferably >95%, more preferably >98% and most preferably >98.5% and measured dry according to EN ISO 11664 4:2010.

In one embodiment, the surface-treated calcium ion-containing material is in form of particles having a BET specific surface area in the range from 2 to 200 $m^2/g$, preferably from 10 to 100 $m^2/g$, and most preferably from 12 to 75 $m^2/g$, measured using nitrogen and the BET method according to ISO 9277:2010.

According to the present invention, the oral care composition comprises the surface-treated magnesium ion-containing material and/or the surface-treated calcium ion-containing material in an amount from 0.1 to 40 wt.-%, based on the total weight of the composition.

According to one embodiment of the present invention, the surface-treated magnesium ion-containing material and/or the surface-treated calcium ion-containing material is present in an amount from 0.1 to 30 wt.-%, preferably from 0.1 to 20 wt. %, more preferably from 0.5 to 15 wt.-%, and most preferably from 0.5 to 10 wt.-%, based on the total weight of the composition.

It is appreciated that the oral care composition is preferably free of nanosized (white) pigment particles such as (nanosized) titanium dioxide.

According to another embodiment, the oral care composition may comprise at least one whitening agent and/or remineralization agent. It is appreciated that such whitening agent is typically not added in order to whiten the oral care composition (as the magnesium ion-containing material) but rather to whiten the tooth.

The whitening agent can be a bleaching agent, an abrasive, or a remineralisation agent, and is preferably selected from the group consisting of hydrogen peroxide, carbamide peroxide, hydroxylapatite, calcium carbonate, and mixtures thereof.

According to one embodiment of the present invention, the at least one remineralisation and/or whitening agent is selected from the group consisting of silica, hydroxylapatite, e.g. nano-hydroxylapatite, calcium carbonate, e.g. amorphous calcium carbonate, ground calcium carbonate, precipitated calcium carbonate, surface-reacted calcium carbonate and combinations thereof, calcium silicate and mixtures thereof.

According to one embodiment, the remineralisation and/or whitening agent preferably has a weight median particle size $d_{50}$ from 10 nm to 100 μm, preferably from 0.1 to 50 μm, more preferably from 1 to 20 μm, and most preferably from 2 to 10 μm.

The at least one remineralisation and/or whitening agent, if present, can be present in the oral care composition in an amount from 1 to 20 wt.-%, preferably from 1.5 to 15 wt.-%, more preferably from 2 to 10 wt.-%, based on the total weight of the composition.

According to one embodiment, the oral care composition of the present invention comprises from 0.1 to 40 wt.-% of the surface-treated magnesium ion-containing material and/or the surface-treated calcium ion-containing material and from 1 to 20 wt.-% of a remineralisation and/or whitening agent, based on the total weight of the composition.

The oral care composition of the present invention can be, for example, a toothpaste, a toothgel, a toothpowder, a varnish, an adhesive gel, a cement, a resin, a spray, a foam, a balm, a composition carried out on a mouthstrip or a buccal adhesive patch, a chewable tablet, a chewable pastille, a chewable gum, a lozenge, a beverage, or a mouthwash.

According to one embodiment of the present invention, the oral care composition is a chewable gum, a lozenge, a toothpaste, a toothpowder, or a mouthwash, and preferably a toothpaste.

According to another preferred embodiment, the oral care composition is a toothpaste, a toothpowder, or a mouthwash and the surface-treated magnesium ion-containing material is in form of particles having a volume median grain diameter ($d_{50}$) of ≥150 nm, preferably from 150 nm to 100 μm, more preferably from 0.2 to 50 μm, even more preferably from 0.3 to 40 μm, and most preferably from 0.4 to 30 μm, as determined by laser diffraction, and a volume determined top cut particle size ($d_{98}$) of equal to or less than 120 μm, preferably from 1 to 100 μm, more preferably from 1 to 90 μm, and most preferably from 1.5 to 80 μm, as determined by laser diffraction, and/or the surface-treated calcium ion-containing material is in form of particles having a volume median grain diameter ($d_{50}$) of ≥150 nm, preferably from 150 nm to 200 μm, more preferably from 0.2 to 35 μm, even more preferably from 0.5 to 30 μm, and most preferably from 1 to 25 μm, as determined by laser diffraction, as determined by laser diffraction, and a volume determined top cut particle size ($d_{98}$) of equal to or less than 3000 μm, preferably from 1 to 600 μm, more preferably from 1 to 400 μm, and most preferably from 1.5 to 250 μm, as determined by laser diffraction.

Preferably, the oral care composition is a toothpaste, a toothpowder, or a mouthwash and the surface-treated magnesium ion-containing material is in form of particles having a volume median grain diameter ($d_{50}$) of from 0.4 to 30 μm, as determined by laser diffraction, and a volume determined top cut particle size ($d_{98}$) of from 1.5 to 80 μm, as determined by laser diffraction, and/or the surface-treated calcium ion-containing material is in form of particles having a volume median grain diameter ($d_{50}$) of from 1 to 25 μm, as determined by laser diffraction, and a volume determined top cut particle size ($d_{98}$) of from 1.5 to 250 μm, as determined by laser diffraction.

According to one embodiment of the present invention, the oral care composition has a pH between 6.8 and 10, preferably between 7.5 and 9 and most preferably between 8 and 9.

The inventive oral care composition can be used in combination with a fluoride compound. The inventors surprisingly found that due to the presence of the surface-treated magnesium ion-containing material and/or the surface-treated calcium ion-containing material in the inventive oral care composition a high availability of fluoride ions in the composition is provided.

According to a preferred embodiment, the oral care composition further comprises a fluoride compound. The fluoride compound is selected from the group consisting of sodium fluoride, stannous fluoride, sodium monofluorophosphate, potassium fluoride, potassium stannous fluoride, sodium fluorostannate, stannous chlorofluoride, amine fluoride, and mixtures thereof. Preferably, the fluoride compound is sodium monofluorophosphate and/or sodium fluoride.

Good results can be achieved by employing an amount of fluoride compound to provide available fluoride ion in the range of 300 to 2 000 ppm in the oral care composition, preferably about 1 450 ppm.

In addition to the surface-treated magnesium ion-containing material and/or the surface-treated calcium ion-containing material, the optional remineralisation and/or whitening agent, and the optional fluoride compound, the oral care composition may further comprise additives typically used in the composition to be prepared, such as bioadhesive polymers, surfactants, binders, humectants, desensitising agents, flavouring agents, sweetening agents and/or water. Such compounds are well known in the art.

According to one embodiment of the present invention, the oral care composition comprises a bioadhesive polymer. The bioadhesive polymer may include any polymer that promotes adhesion of any of the components of the oral care composition to teeth or tooth surface and remains on the teeth or tooth surface for an extended period of time, for example, 1 hour, 3 hours, 5 hours, 10 hours or 24 hours. In certain embodiments, the bioadhesive polymer may become more adhesive when the oral care composition is moistened with, for example, water or saliva. In other embodiments, the bioadhesive polymer is a material or combination of materials that enhance the retention of the active ingredient on the teeth or a tooth surface onto which the composition is applied. Such bioadhesive polymers include, for example, hydrophilic organic polymers, hydrophobic organic polymers, silicone gums, silicas, and combinations thereof. According to one embodiment, the bioadhesive polymer is selected from the group consisting of hydroxyethyl methacrylate, PEG/PPG copolymers, polyvinylmethylether/maleic anhydride copolymers, polyvinylpyrrolidone (PVP), cross-linked PVP, shellac, polyethylene oxide, methacrylates, acrylates copolymers, methacrylic copolymers, vinylpyrrolidone/vinyl acetate copolymers, polyvinyl caprolactum, polylactides, silicone resins, silicone adhesives, chitosan, milk proteins (casein), amelogenin, ester gum, and combinations thereof.

Suitable surfactants are generally anionic organic synthetic surfactants throughout a wide pH range. Representative of such surfactants used in the range of about 0.5 to 5 wt. %, based on the total weight of the oral care composition, are water-soluble salts of $C_{10}$-$C_{18}$ alkyl sulphates, such as sodium lauryl sulphate, of sulphonated monoglycerides of fatty acids, such as sodium monoglyceride sulphonates, of fatty acid amides of taurine, such as sodium N-methyl-N-palmitoyltauride, and of fatty acid esters of isethionic acid, and aliphatic acylamides, such as sodium N-lauroyl sarcosinate. However, surfactants obtained from natural sources such as cocamidopropyl betaine may also be used.

Suitable binders or thickening agents to provide the desired consistency are, for example, hydroxyethylcellulose, sodium carboxymethylcellulose, natural gums, such as gum karaya, gum arabic, gum tragacanth, xanthan gum or cellulose gum. Generally, from 0.5 to 5 wt. %, based on the total weight of the oral care composition, can be used.

Desensitising agents can be selected from the group consisting of potassium nitrate, gluteraldehyde, silver nitrate, zinc chloride, strontium chloride hexahydrate, sodium fluoride, stannous fluoride, strontium chloride, strontium acetate, arginine, hydroxylapatite, calcium sodium phosphosilicate, potassium oxalate, calcium phosphate, calcium carbonate, bioactive glasses, and mixtures thereof.

Various humectants known to the skilled person can be used, such as glycerine, sorbitol and other polyhydric alcohols, for example, in an amount from 20 to 40 wt. %, based on the total weight of the oral care composition. Examples of suitable flavouring agents include oil of wintergreen, oil of spearmint, oil of peppermint, oil of clove, oil of *sassafras* and the like. Saccharin, aspartame, dextrose, or levulose can be used as sweetening agents, for example, in an amount from 0.01 to 1 wt.-%, based on the total weight of the oral care composition. Preservatives such as sodium benzoate may be present in an amount from 0.01 to 1 wt.-%, based on the total weight of the oral care composition. Colorants may also be added to the oral care composition, for example, in an amount from 0.01 to 1.5 wt.-%, based on the total weight of the oral care composition.

According to one embodiment of the present invention, the oral care composition is a toothpaste. The toothpaste may be produced by a method comprising the following steps:

I) providing a mixture of water and humectant(s), and optionally at least one of a thickener, a preservative, a fluoride compound, and a sweetener, II) adding the surface-treated magnesium ion-containing material and/or the surface-treated calcium ion-containing material in an amount from 0.1 to 40 wt. %, based on the total weight of the composition, and optionally a colorant, to the mixture of step I), III) adding a surfactant to the mixture of step II), and IV) optionally, adding a flavouring agent to the mixture of step III).

However, a toothpaste of the present invention may also be produced by any other method known to the skilled person.

The oral care composition of the present invention may be used in professional, in office treatment or in at home treatment.

According to one embodiment, the oral care composition is used in a method comprising the step of administering to at least one tooth of a patient a therapeutically effective amount of the oral care composition at least once a day, preferably twice a day and more preferably three-times a day. A "therapeutically effective" amount of the oral care composition is an amount that is sufficient to have the desired therapeutic or prophylactic effect in the human subject to whom the composition is administered, without undue adverse side effects (such as toxicity, irritation, or allergic response), commensurate with a reasonable benefit/risk ratio when used in the manner of this invention. The specific effective amount will vary with such factors as the particular condition being treated, the physical condition of the subject, the nature of concurrent therapy (if any), the specific dosage form, and the specific oral care composition employed.

According to one embodiment, the oral care composition of the present invention is used in a method comprising the step of applying the composition to at least one tooth of a patient for an effective amount of time, preferably the composition remains on the at least one tooth for at least 1 min, at least 15 min, at least 30 min, at least 1 hour, at least 2 hours, at least 12 hours or at least 24 hours.

According to a preferred embodiment of the present invention, the oral care composition does not contain an oxidative whitening compound.

The Use

It was found that a surface-treated magnesium ion-containing material and/or a surface-treated calcium ion-containing material according to the present invention can be used as opacifying agent and/or whitening pigment in oral care compositions.

According to one embodiment of the present invention, a surface-treated magnesium ion-containing material is provided that can be used as opacifying agent in oral care compositions.

According to another embodiment of the present invention, a surface-treated magnesium ion-containing material is provided that can be used as whitening pigment in oral care compositions.

According to another embodiment of the present invention, a surface-treated magnesium ion-containing material is provided that can be used as opacifying agent and whitening pigment in oral care compositions.

According to one embodiment of the present invention, a surface-treated calcium ion-containing material is provided that can be used as opacifying agent in oral care compositions.

According to another embodiment of the present invention, a surface-treated calcium ion-containing material is provided that can be used as whitening pigment in oral care compositions.

According to another embodiment of the present invention, a surface-treated calcium ion-containing material is provided that can be used as opacifying agent and whitening pigment in oral care compositions.

According to one embodiment of the present invention, a surface-treated magnesium ion-containing material and a surface-treated calcium ion-containing material is provided that can be used as opacifying agent in oral care compositions.

According to another embodiment of the present invention, a surface-treated magnesium ion-containing material and a surface-treated calcium ion-containing material is provided that can be used as whitening pigment in oral care compositions.

According to another embodiment of the present invention, a surface-treated magnesium ion-containing material and a surface-treated calcium ion-containing material is provided that can be used as opacifying agent and whitening pigment in oral care compositions.

With regard to the definition of the surface-treated magnesium ion-containing material, the surface-treated calcium ion-containing material, the oral care composition, and preferred embodiments thereof, reference is made to the statements provided above when discussing the technical details of the surface-treated magnesium ion-containing material and the oral care composition of the present invention.

It is appreciated that the surface-treated magnesium ion-containing material and/or the surface-treated calcium ion-containing material can be used as whitening pigment and thus is intended to impart whiteness to the oral care composition, i.e. the surface-treated magnesium ion-containing material and/or the surface-treated calcium ion-containing material does not whiten the teeth.

It was surprisingly found by the inventors that the surface-treated magnesium ion-containing material and/or the surface-treated calcium ion-containing material also provides a high availability of fluoride ions in an oral care composition. In particular, the availability of fluoride ions is higher compared to oral care compositions comprising calcium carbonate which is not surface-treated according to the present invention.

Thus, the present invention refers in a further aspect to a surface-treated magnesium ion-containing material and/or surface-treated calcium ion-containing material that can be used for improving the availability of fluoride ions in oral care compositions, especially compared to oral care compositions comprising calcium carbonate which is not surface-treated according to the present invention.

According to one embodiment of the present invention, a surface-treated magnesium ion-containing material is provided that can be used for improving the availability of fluoride ions in oral care compositions, especially compared to oral care compositions comprising calcium carbonate which is not surface-treated according to the present invention.

According to another embodiment of the present invention, a surface-treated calcium ion-containing material is provided that can be used for improving the availability of fluoride ions in oral care compositions, especially compared to oral care compositions comprising calcium carbonate which is not surface-treated according to the present invention.

According to another embodiment of the present invention, a surface-treated magnesium ion-containing material and a surface-treated calcium ion-containing material are provided that can be used for improving the availability of fluoride ions in oral care compositions, especially compared to oral care compositions comprising calcium carbonate which is not surface-treated according to the present invention.

The scope and interest of the present invention will be better understood based on the following examples which are intended to illustrate certain embodiments of the present invention and are non-limitative.

EXAMPLES

1. Measurement Methods

In the following, measurement methods implemented in the examples are described.

Particle Size Distribution

Volume determined median particle size $d_{50}$(vol) and the volume determined top cut particle size $d_{98}$(vol) was evaluated using a Malvern Mastersizer 3000 Laser Diffraction System (Malvern Instruments Plc., Great Britain) equipped with a Hydro LV system. The $d_{50}$(vol) or dos (vol) value indicates a diameter value such that 50% or 98% by volume, respectively, of the particles have a diameter of less than this value. The powders were suspended in 0.1 wt.-% $Na_4O_7P_2$ solution. 10 ml of 0.1 wt.-% $Na_4O_7P_2$ was added to the Hydro LV tank, then the sample slurry was introduced until an obscuration between 10-20% was achieved. Measurements were conducted with red and blue light for 10 s each. For the analysis of the raw data, the models for non-spherical particle sizes using Mie theory was utilized, and a particle refractive index of 1.57, a density of 2.70 g/cm$^3$, and an absorption index of 0.005 was assumed. The methods and instruments are known to the skilled person and are commonly used to determine particle size distributions of fillers and pigments.

Specific Surface Area (SSA)

The specific surface area was measured via the BET method according to ISO 9277:2010 using nitrogen as adsorbing gas on a Micromeritics ASAP 2460 instrument from Micromeritics. The samples were pretreated in vacuum (10-5 bar) by heating at 150° C. for a period of 60 min prior to measurement.

CIELAB L* of Particulate Materials

The CIELAB L* of the magnesium ion-containing material and other particulate materials was measured dry in accordance with EN ISO 11664 4:2010.

Fluoride Availability

A toothpaste was freshly prepared as oral care composition and aged overnight (14 h) to establish short-term equilibration of the fluoride concentration (i.e. fluoride availability). Extraction was conducted by diluting the toothpaste with the 10-fold equivalent of demineralized water (typically 3-5 g of toothpaste diluted with 30 50 g water) in a glass beaker, followed by vigorous stirring at 800 rpm for 1 h, and filtration through a syringe filter (Chromafil Xtra, RC-20/25 0.2 μm). Fluoride availabilities were determined after volumetric dilution (Eppendorf Research Plus micropipettes) by a factor of 100 using cuvette tests (Hach Lange LCK 323, Fluoride 0.1-2.5 ppm) in a Hach-Lange DR6000 spectrophotometer. The weighted-in quantities for all dilutions were recorded and the effective (free) fluoride concentrations (i.e. the fluoride availability) in the original formulations were calculated using these values. The percentage of extractable fluoride was reported with respect to a benchmark experiments with unmodified (base formulation) toothpaste, which were conducted for each series of experiments. The result attained with the unmodified toothpaste was multiplied by 0.98 to account for the dilution of the toothpaste by the addition of the mineral. Some samples were added as filter cakes with solids contents between 10-85 wt.-%, the occurring dilution was accounted for in the calculation of the fluoride availability.

Whiteness/CIELAB L* of Oral Care Compositions

The corresponding toothpaste was transferred into a PTFE sample holder and subsequently covered with a glass plate to attain a reproducible, flat surface. The samples were evaluated in a Datacolor ELREPHO spectrophotometer using barium sulfate as reference material. The values reported for whiteness are the L* lightness values of the CIELAB color space according to EN ISO 11664 4:2010.

Opacity of Oral Care Compositions

The corresponding toothpaste was diluted with 15 wt. % of demineralized water and mixed on a speed mixer (Hauschild DAC 150.1 FVZ) for 20 s at 2760 rpm. Subsequently, a 300 μm layer was spread out on a Leneta Opacity Chart (Form 3B-H) using a TQC AFA Compact automatic film applicator with 23 mm s$^{-1}$. The film was immediately covered with clear plastic sheets to prevent drying. The contrast value ($R_{y,black}/R_{y,white}$*100) was calculated based on the average of three separate measurements of $R_y$ per area in a Datacolor 800V spectrophotometer using barium sulfate as reference.

Amount of Surface-Treatment Layer

The amount of the treatment layer on the magnesium and/or calcium ion-containing material is calculated theoretically from the values of the BET of the untreated magnesium and/or calcium ion-containing material and the amount of the one or more compound(s) that is/are used for the surface-treatment. It is assumed that 100% of the one or more compound(s) are present as surface treatment layer on the surface of the magnesium and/or calcium ion-containing material.

2. Materials Used and Preparation of Toothpastes

The particulate materials set out in table 1 have been used as base materials for the present invention.

TABLE 1 particulate materials used as base materials

| Base material | Name | Description | Supplier or tradename |
|---|---|---|---|
| #M1 | PHM | Precipitated hydromagnesite (PHM) | Omya International |
| #M2 | PCC | Precipitated calcium carbonate | Omya International |
| #M3 | SRCC | Surface-reacted calcium carbonate | Omya International |
| #M4 | Dolomite | Micronized dolomite, coarse | Omya International |
| #M5 | Dolomite 2 | Micronized dolomite, fine | Omya International |

The characteristics of the particulate materials are set out in the following table 2.

TABLE 2 characteristics of the particulate materials used as base materials

| Base material | $S_{BET}$/m$^2$ g$^{-1}$ | $d_{50}$/μm | $d_{98}$/μm |
|---|---|---|---|
| #M1 | 25 | 25 | 73 |
| #M2 | 22 | 2.9 | 249* |
| #M3 | 59 | 6.8 | 15 |
| #M4 | 3.2 | 3.3 | 11 |
| #M5 | 16 | 0.5 | 1.8 |

*forms artefacts of incomplete deagglomerates in lab scale

The surface-treated materials are prepared according to the methods set out in the following table 3.

TABLE 3 preparation of the surface-treated materials

| Surface-treated material | Base material | Treatment method | Treatment agent | Quantity of treatment agent |
|---|---|---|---|---|
| #S1 | #M1 | #P1 | #A1 | 15 |
| #S2 | #M1 | #P1 | #A1 | 0.03 |
| #S3 | #M1 | #P1 | #A1 | 0.3 |
| #S4 | #M1 | #P1 | #A1 | 1 |
| #S5 | #M1 | #P1 | #A1 | 3 |
| #S6 | #M1 | #P1 | #A1 | 6 |
| #S7 | #M1 | #P1 | #A1 | 9 |
| #S8 | #M1 | #P1 | #A2 | 1 |
| #S9 | #M1 | #P1 | #A2 | 3 |
| #S10 | #M1 | #P1 | #A3 | 25 |
| #S11 | #M1 | #P1 | #A4 | 8.3 |
| #S12 | #M1 | #P1 | #A4 | 1 |
| #S13 | #M1 | #P1 | #A4 | 3 |
| #S14 | #M1 | #P1 | #A4 | 6 |

TABLE 3-continued preparation of the surface-treated materials

| Surface-treated material | Base material | Treatment method | Treatment agent | Quantity of treatment agent |
|---|---|---|---|---|
| #S15 | #M1 | #P1 | #A4 | 9 |
| #S16 | #M1 | #P1[a] | #A1 + #A4 | 3 + 3 |
| #S17 | #M1 | #P1[b] | 1. #A4 | 3 |
| | | | 2. #A1 | 3 |
| #S18 | #M1 | #P1 | #A5 | 3 |
| #S19 | #M1 | #P1 | #A6 | 3 |
| #S20 | #M1 | #P1 | #A7 | 3 |
| #S21 | #M1 | #P1 | #A8 | 3 |
| #S22 | #M1 | #P1 | #A9 | 3 |
| #S23 | #M1 | #P1 | #A10 | 3 |
| #S24 | #M1 | #P1 | #A11 | 3 |
| #S25 | #M1 | #P3 | #A1 | 3 |
| #S26 | #M1 | #P3 | #A1 | 0.3 |
| #S27 | #M1 | #P3[a] | #A1 + #A4 | 0.3 + 0.3 |
| #S28 | #M1 | #P4 | #A12 | 20 |
| #S29 | #M1 | #P4 | #A13 | 20 |
| #S30 | #M2 | #P1 | #A1 | 7.6 |
| #S31 | #M2 | #P1 | #A4 | 4.3 |
| #S32 | #M2 | #P2 | #A14 | 15 |
| #S33 | #M2 | #P4 | #A12 | 15 |
| #S34 | #M3 | #P1 | #A1 | 15 |
| #S35 | #M3 | #P1 | #A3 | 32 |
| #S36 | #M3 | #P2 | #A14 | 15 |
| #S37 | #M3 | #P4 | #A12 | 20 |
| #S38 | #M3 | #P4 | #A13 | 20 |
| #S39 | #M4 | #P1 | #A11 | 3 |
| #S40 | #M5 | #P1 | #A15 | 1 |
| #S41 | #M5 | #P1 | #A15 | 3 |
| #S42 | #M5 | #P1 | #A15 | 8 |
| #S43 | #M4 | #P1 | #A16 | 8.3 |
| #S44 | #M4 | #P1 | #A17 | 8.3 |

[a]Treatment conducted with two reagents (simultaneous addition).
[b]Treatment conducted with two reagents (sequential addition).

The treatment methods set out in table 3 are further described in table 4 as follows:

TABLE 4 surface treatment methods

| # | Surface treatment method |
|---|---|
| P1 | Wet-treatment of the base materials<br>A slurry comprising about 60 g of mineral in 600 g of demineralized water was prepared. To this slurry, the desired quantity of the desired surface treatment agent was added over 15 min. If applicable, the desired quantity of the desired second surface treatment agent was added over 15 min. The resulting slurry was stirred for 1 h at room temperature and subsequently filtered over a Buchner-funnel, dried in an oven at 80° C. and deagglomerated using a mortar. |
| P2 | Wet-coating of the base materials<br>A slurry comprising the desired quantity of the treatment agent in 2.5 L water was prepared and heated to 85° C. under gentle agitation (200-300 rpm). To this solution, 100 g of the mineral was added and stirred for 1 h. The slurry was transferred into a tray, dried in a convection oven (110° C.) and deagglomerated using a mortar. |
| P3 | Spray-coating of the base materials<br>A slurry comprising 300 g of the mineral in 2800 g of demineralized water was prepared. To this slurry 200 g of a solution containing the desired quantity of the desired surface treatment agent was added over 15 min. The resulting slurry was stirred for 1 h at room temperature and subsequently spray-dried in a GEA Niro A/S spray dryer with an inlet temperature of ca. 270° C., and an outlet temperature of ca. 110° C. |
| P4 | Dry-coating of the base materials<br>100 g of mineral were prepared in a high-speed mixer (Somakon MP-LB Mixer, 2.5 L, Somakon Verfahrenstechnik, Germany) |

TABLE 4-continued surface treatment methods

| # | Surface treatment method |
|---|---|
| | and preheated to the desired coating temperature (80-120° C.) while mixing at 300 rpm. Over 5-10 minutes, the desired quantity of the desired surface treatment agent was added, and the system stirred for a further 10 min. Then, the powder was allowed to cool without further agitation. |

The surface treatment agents were as described in table 5 below.

TABLE 5 surface treatment agents used

| # | Treatment agent | Supplier | Description |
|---|---|---|---|
| A1 | Citric acid, monobasic | Simga-Aldrich | Citric acid sodium salt |
| A2 | Citric acid, tribasic | Sigma-Aldrich | Citric acid sodium salt |
| A3 | Valeric acid | Sigma-Aldrich | Carboxylic acid |
| A4 | Sodium phosphate, dibasic | Sigma-Aldrich | Phosphoric acid sodium salt |
| A5 | Succinic acid | Sigma-Aldrich | Organic acid |
| A6 | Maleic acid | Sigma-Aldrich | Dicarboxylic acid |
| A7 | Malonic acid | Sigma-Aldrich | Dicarboxylic acid |
| A8 | L-(+)-Tartaric acid | Sigma-Aldrich | Dicarboxylic acid |
| A9 | Adipic acid | Sigma-Aldrich | Dicarboxylic acid |
| A10 | Fumaric acid | Sigma-Aldrich | Dicarboxylic acid |
| A11 | Oxalic acid | Sigma-Aldrich | Dicarboxylic acid |
| A12 | Lanolin | Sigma-Aldrich | Natural wax |
| A13 | PPG 4000 | Sigma-Aldrich | Polypropylene glycol |
| A14 | Cekol 2000 | CP Kelco | Carboxymethylcellulose |
| A15 | Sodium polyphosphate | Sigma-Aldrich | Polyphosphate*, sodium salt |
| A16 | Tetraethyl orthosilicate | Sigma-Aldrich | Tetraethoxysilane |
| A17 | Sodium water glass | Sigma-Aldrich | Sodium silicate solution |

*n in the formula $M_{(n+2)}P_nO_{(3n+1)}$ is an integer from 10 to 15

The surface-treated materials had the characteristics set out in the following table 6.

TABLE 6 characteristics of the surface-treated materials

| Surface-treated materials | $S_{BET}$/m$^2$ g$^{-1}$ | $d_{50}$/μm | $d_{98}$/μm |
|---|---|---|---|
| #S1 | 19 | 29 | 335* |
| #S2 | 25 | 24 | 257* |
| #S3 | 27 | 24 | 75 |
| #S4 | 28 | 25 | 74 |
| #S5 | 29 | 25 | 78 |
| #S6 | 28 | 25 | 80 |
| #S7 | 29 | 35 | 424* |
| #S8 | 32 | 23 | 67 |
| #S9 | 29 | 24 | 70 |
| #S11 | 30 | 24 | 79 |
| #S12 | 28 | 24 | 71 |
| #S13 | 22 | 27 | 376* |
| #S14 | 50 | 25 | 99 |
| #S15 | 31 | 28 | 529* |
| #S16 | 24 | 24 | 343* |
| #S17 | 21 | 24 | 343* |
| #S18 | 28 | 23 | 67 |
| #S19 | 49 | 24 | 68 |
| #S20 | 25 | 24 | 67 |
| #S21 | 34 | 25 | 67 |
| #S22 | 44 | 25 | 70 |
| #S23 | 43 | 25 | 69 |
| #S24 | 42 | 25 | 70 |
| #S25 | 27 | 21 | 59 |
| #S26 | 24 | 21 | 59 |
| #S27 | 25 | 21 | 58 |

TABLE 6-continued characteristics of the surface-treated materials

| Surface-treated materials | $S_{BET}$/m$^2$ g$^{-1}$ | $d_{50}$/μm | $d_{98}$/μm |
|---|---|---|---|
| #S28 | 9 | — | — |
| #S29 | 10 | 25 | 71 |
| #S30 | 15 | 2.3 | 70 |
| #S31 | 18 | 21 | 232* |
| #S32 | 14 | 2.8 | 120 |
| #S33 | 7 | — | — |
| #S34 | 53 | 10 | 576* |
| #S35 | —[a] | —[a] | —[a] |
| #S36 | 42 | 177 | 2800* |
| #S37 | 19 | — | — |
| #S38 | 19 | 6.4 | 14 |
| #S39 | 5 | 3.7 | 66 |
| #S40 | 16 | 0.6 | 2.2 |
| #S41 | 17 | 0.5 | 2.4 |
| #S42 | 17 | 0.5 | 1.9 |
| #S43 | 6 | 2.7 | 590* |
| #S44 | 6 | 2.5 | 8.4 |

*forms artefacts of incomplete deagglomerates in lab scale
[a]no characterization was made due to smell of product.

For the preparation of a toothpaste base formulation, an IKA ULTRA TURRAX® disperser was used. The ingredients in the toothpaste base formulation are listed in the following table 7. The formulations were prepared with 1 kg total mass. In a beaker, sorbitol, sodium fluoride, sodium saccharin, sodium benzoate, propylene glycol and glycerin and cellulose gum were vigorously mixed. Subsequently, water was added and the mixture further agitated until a homogeneous texture was attained. Then, Sorbosil AC35 was added step-wise under strong agitation and further stirred until a homogeneous texture was attained. Then, Sorbosil TC15 was added step-wise under strong agitation and further stirred until a homogeneous texture was attained to obtain the toothpaste base formulation. Four master batches of toothpaste were prepared based on different batches of raw materials. To compensate for the occurring differences (particularly in the optical properties) they will be differentiated as batch 1 (#B1), batch 2 (#B2), batch 3 (#B3) and batch 4 (#B4).

TABLE 7

Recipe of the toothpaste base formulation.

| # | Ingredient | Quantity/ mass equiv. |
|---|---|---|
| I1 | sorbitol 70% | 23.67 |
| I2 | demineralized water | 25.85 |
| I3 | Phoskadent NaF | 0.34 |
| I4 | sodium saccharin | 0.11 |
| I5 | sodium benzoate | 0.11 |
| I6 | propylene glycol | 10.76 |
| I7 | glycerol | 10.76 |
| I8 | cellulose gum | 0.86 |
| I9 | Sorbosil AC35 silica | 21.52 |
| I10 | Sorbosil TC15 silica | 6.02 |
| I11 | sodium lauryl sulfate (15 wt. % solution) | 1.25 |
| I12 | aroma spearmint | 0.80 |

The final toothpaste was prepared in a plastic container by adding the desired quantity of the corresponding base material or surface-treated material (0.25-2 g) to 25-30 g of the toothpaste base formulation. The formulations were manually mixed using a spatula, and subsequently homogenized using either a speed mixer (Hauschild DAC 150.1 FVZ) for 20 s at 2760 rpm or a Polytron GT 10-35 PT disperser equipped with a PT-DA 30/2EC-F250 dispersing aggregate. Subsequently, the desired quantity of surfactant (111 according to the base formulation recipe in table 7) was added using an Eppendorf Research Plus micropipette and the formulation were mixed manually using a spatula. Finally, the desired quantity of flavour (112 according to the base formulation recipe in table 7) was added using an Eppendorf Research Plus micropipette and the formulation was mixed manually using a spatula.

3. Results

The toothpastes prepared were evaluated with respect to the fluoride availability, the whiteness and opacity. The results are set out in the following table 8.

TABLE 8 results

| Surface-treated material | Base formulation | Surface-treated material quantity/wt. % | Fluoride availability/% | Whiteness CIELAB L*/— — | Opacity Contrast value/— — |
|---|---|---|---|---|---|
| — | #B1 | 0 | 100 | 73.2 | 2.8 |
| — | #B2 | 0 | 100 | 79.3 | 2.7 |
| — | #B3 | 0 | 100 | 83.0 | 2.8 |
| — | #B4 | 0 | 100 | — | 2.9 |
| #S1 | #B1 | 2.00 | 91 | 83.0 | 5.3 |
| #S2 | #B2 | 1.86 | 81 | 83.8 | 4.6 |
| #S3 | #B2 | 1.93 | 84 | 83.6 | 4.7 |
| #S4 | #B2 | 1.99 | 84 | 84.3 | 4.8 |
| #S5 | #B2 | 1.91 | 83 | 84.1 | 4.6 |
| #S6 | #B2 | 1.90 | 77 | 83.9 | 4.8 |
| #S7 | #B2 | 1.90 | 74 | 83.9 | 4.9 |
| #S8 | #B2 | 1.96 | 80 | 83.7 | 4.7 |
| #S9 | #B2 | 1.87 | 83 | 83.2 | 4.4 |
| #S10 | #B1 | 1.92 | 79 | 83.8 | 4.9 |
| #S11 | #B1 | 1.88 | 91 | 83.5 | 5.2 |
| #S12 | #B2 | 1.97 | 83 | 83.9 | 4.5 |
| #S13 | #B2 | 1.99 | 89 | 83.3 | 4.7 |
| #S14 | #B2 | 1.90 | 91 | 82.3 | 3.5 |
| #S15 | #B2 | 1.93 | 89 | 83.9 | 4.4 |
| #S16 | #B2 | 1.91 | 76 | 84.1 | 4.6 |
| #S17 | #B2 | 2.00 | 92 | 84.1 | 4.5 |
| #S18 | #B2 | 1.92 | 83 | 83.5 | 4.4 |
| #S19 | #B2 | 2.02 | 80 | 83.0 | 4.2 |
| #S20 | #B2 | 1.98 | 86 | 83.6 | 4.4 |
| #S21 | #B2 | 1.95 | 88 | 83.5 | 4.1 |
| #S22 | #B2 | 1.91 | 83 | 83.3 | 4.0 |
| #S23 | #B2 | 1.89 | 89 | 83.2 | 4.1 |
| #S24 | #B2 | 1.97 | 91 | 82.8 | 4.0 |
| #S25 | #B2 | 2.00 | 87 | 83.6 | 4.7 |
| #S26 | #B2 | 2.00 | 78 | 84.0 | 5.0 |
| #S27 | #B2 | 1.90 | 87 | 83.5 | 4.4 |
| #S28 | #B1 | 1.92 | 85 | 83.5 | 5.0 |
| #S29 | #B1 | 1.93 | 87 | 83.4 | 4.8 |
| #S30 | #B1 | 2.01 | 49 | 85.4 | 7.5 |
| #S31 | #B1 | 2.01 | 49 | 85.4 | 7.8 |
| #S32 | #B1 | 1.92 | 48 | 86.5 | 7.6 |
| #S33 | #B1 | 1.94 | 49 | 85.6 | 7.3 |
| #S34 | #B1 | 1.98 | 57 | 82.0 | 5.1 |
| #S35 | #B1 | 1.90 | 50 | 82.0 | 4.7 |
| #S36 | #B1 | 1.94 | 54 | 81.7 | 4.5 |
| #S37 | #B1 | 1.96 | 50 | 82.2 | 4.5 |
| #S38 | #B1 | 1.92 | 50 | 81.9 | 4.8 |
| #S39 | #B2 | 1.97 | 94 | 83.9 | n/a |
| #S40 | #B3 | 2.02 | 79 | 84.7 | 10.6 |
| #S41 | #B3 | 1.96 | 90 | 85.6 | 11 |
| #S42 | #B3 | 2.04 | 92 | 85.7 | 9.5 |
| #S43 | #B4 | 2.00 | 92 | — | 7.2 |
| #S44 | #B4 | 2.00 | 83 | — | 7.0 |

The results of the materials being not surface-treated (base materials) are set out for comparison reasons in the following table 9.

TABLE 9 results of the base materials (comparative examples)

| Base Material | Base formulation | Base Material quantity/ wt. % | Fluoride availability/% | Whiteness CIELAB L*/— — | Opacity Contrast value/— — |
|---|---|---|---|---|---|
| — | #B1 | 0 | 100 | 73.2 | 2.8 |
| — | #B2 | 0 | 100 | 79.3 | 2.7 |
| #M1 | #B1 | 1.94 | 81 | 83.5 | 5.2 |
| #M1 | #B1 | 2.94 | — | 82.1 | 7.3 |
| #M1 | #B1 | 3.80 | — | 82.3 | 9.4 |
| #M1 | #B1 | 5.82 | — | 85.1 | 12.6 |
| #M1 | #B2 | 1.87 | 82 | 84.1 | 4.7 |
| #M2 | #B1 | 2.03 | 46 | 85.5 | 8.8 |
| #M3 | #B1 | 1.85 | 48 | 82.2 | 4.2 |
| #M4 | #B2 | 1.92 | 94 | 84.7 | 5.5 |
| #M5 | #B3 | 1.98 | 78.3 | 80.9 | 8.7 |

From the results, it can be gathered that the surface-treated materials according to the present invention provide high fluoride availability in combination with high whiteness and opacity.

The invention claimed is:

1. A surface-treated magnesium ion-containing material obtained by treating a surface of a magnesium ion-containing material with;

wherein the magnesium ion-containing material is hydromagnesite ($Mg_5(CO_3)_4(OH)_2 \cdot 4H_2O$); and wherein the magnesium ion-containing material prior to surface treatment is in form of particles having a BET specific surface area in a range from 2 to 200 $m^2/g$, measured using nitrogen and a BET method according to ISO 9277:2010.

2. The surface-treated magnesium ion-containing material according to claim 1, wherein the magnesium ion-containing material prior to surface treatment is in form of particles having a) a volume median grain diameter ($d_{50}$) of ≥150 nm, as determined by laser diffraction, and/or b) a volume determined top cut particle size ($d_{98}$) of equal to or less than 100 μm, as determined by laser diffraction.

3. The surface-treated magnesium ion-containing material according to claim 1, wherein the surface-treated magnesium ion-containing material is obtained by treating the surface of the magnesium ion-containing material with phosphoric acid in an amount from 0.1 to 25 wt.-%, based on a total dry weight of the magnesium ion-containing material.

4. The surface-treated magnesium ion-containing material according to claim 1, wherein the magnesium ion-containing material prior to surface treatment is in form of particles having a) a volume median grain diameter ($d_{50}$) from 150 nm to 40 μm as determined by laser diffraction, and b) a volume determined top cut particle size ($d_{98}$) from 1 to 90 μm as determined by laser diffraction.

5. The surface-treated magnesium ion-containing material according to claim 1, wherein the magnesium ion-containing material prior to surface treatment is in form of particles having a) a volume median grain diameter ($d_{50}$) from 0.3 μm to 30 μm as determined by laser diffraction, and b) a volume determined top cut particle size ($d_{98}$) from 1.5 to 85 μm as determined by laser diffraction.

6. The surface-treated magnesium ion-containing material according to claim 1, wherein the magnesium ion-containing material prior to surface treatment is in form of particles having a) a volume median grain diameter ($d_{50}$) from 0.4 μm to 27 μm as determined by laser diffraction, and b) a volume determined top cut particle size ($d_{98}$) from 1.5 to 80 μm as determined by laser diffraction.

7. The surface-treated magnesium ion-containing material according to claim 1, wherein the magnesium ion-containing material prior to surface treatment is in form of particles having a BET specific surface area in the range from 3 to 75 $m^2/g$, measured using nitrogen and the BET method according to ISO 9277:2010.

8. An oral care composition comprising:

a surface-treated magnesium ion-containing material according to claim 1; and optionally, a surface-treated calcium ion-containing material obtained by treating a surface of a calcium ion-containing material with one or more compound(s) selected from the group consisting of a polyphosphate, a carboxylic acid containing up to six carbon atoms, a di-, and tri-carboxylic acid containing up to six carbon atoms where carboxylic acid groups are linked by a chain of 0-4 intermittent carbon atoms a water-insoluble polymer, a water-insoluble wax, a silicate- and/or aluminate-group containing compound, and a corresponding salt thereof.

9. The oral care composition according to claim 8, wherein the oral care composition further comprises a fluoride compound.

10. The oral care composition according to claim 8, wherein the oral care composition further comprises a remineralisation and/or whitening agent.

11. The oral care composition according to claim 8, wherein the oral care composition is a toothpaste, a toothgel, a toothpowder, a varnish, an adhesive gel, a cement, a resin, a spray, a foam, a balm, a composition carried out on a mouthstrip or a buccal adhesive patch, a chewable tablet, a chewable pastille, a chewable gum, a lozenge, a beverage, or a mouthwash.

12. The oral care composition according to claim 8, wherein the oral care composition has a pH between 6.8 and 10.

13. The oral care composition according to claim 8, wherein the oral care composition comprises the surface-treated magnesium ion-containing material and/or the surface-treated calcium ion-containing material in an amount from 0.1 to 40 wt.-%, based on a total weight of the oral care composition.

14. A method of making an oral care composition, comprising steps of:

adding a surface-treated magnesium ion-containing material according to claim 1 to the oral care composition as an opacifying agent and/or a whitening pigment; and optionally, adding a surface-treated calcium ion-containing material to the oral care composition, wherein the surface-treated calcium ion-containing material is obtained by treating the surface of a calcium ion-containing material with one or more compound(s) selected from the group consisting of a polyphosphate, a carboxylic acid containing up to six carbon atoms, a di-, and tri-carboxylic acid containing up to six carbon atoms where carboxylic acid groups are linked by a chain of 0-4 intermittent carbon atoms, a water-insoluble polymer, a water-insoluble wax, a silicate-and/or aluminate-group containing compound, and a corresponding salt thereof.

15. A method of improving availability of fluoride ions in an oral care composition, comprising steps of:

adding a surface-treated magnesium ion-containing material according to claim 1 to the oral care composition; and optionally, adding a surface-treated calcium ion-containing material to an oral care composition, wherein the surface-treated calcium ion-containing material is obtained by treating the surface of a calcium ion-containing material with one or more compound(s) selected from the group consisting of a polyphosphate, a carboxylic acid containing up to six carbon atoms, a di-, and tri-carboxylic acid containing up to six carbon atoms where carboxylic acid groups are linked by a chain of 0-4 intermittent carbon atoms, a water-insoluble polymer, a water-insoluble wax, a silicate-and/or aluminate-group containing compound, and a corresponding salt thereof.

* * * * *